(12) United States Patent
Horiguchi et al.

(10) Patent No.: US 7,998,684 B2
(45) Date of Patent: Aug. 16, 2011

(54) SCREENING METHOD FOR AN AGENT FOR TREATMENT OF NEURODEGENERATIVE DISEASE

(75) Inventors: Takashi Horiguchi, Osaka (JP); Tomomichi Watanabe, Osaka (JP); Yasushi Shintani, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 615 days.

(21) Appl. No.: 11/883,791

(22) PCT Filed: Feb. 6, 2006

(86) PCT No.: PCT/JP2006/302404
§ 371 (c)(1),
(2), (4) Date: Aug. 7, 2007

(87) PCT Pub. No.: WO2006/083042
PCT Pub. Date: Aug. 10, 2006

(65) Prior Publication Data
US 2008/0161239 A1    Jul. 3, 2008

(30) Foreign Application Priority Data
Feb. 7, 2005    (JP) ................................. 2005-030097

(51) Int. Cl.
*G01N 33/53* (2006.01)

(52) U.S. Cl. ........................................................ 435/7.1

(58) Field of Classification Search .................... None
See application file for complete search history.

(56) References Cited

U.S. PATENT DOCUMENTS

| | | | | |
|---|---|---|---|---|
| 5,187,153 | A * | 2/1993 | Cordell et al. ................... | 514/12 |
| 6,720,181 | B1 * | 4/2004 | Chiaur et al. ................. | 435/325 |
| 2003/0092603 | A1 * | 5/2003 | Mundy et al. ..................... | 514/1 |

FOREIGN PATENT DOCUMENTS

| | | |
|---|---|---|
| EP | 1 428 891 A1 | 6/2004 |
| WO | 00/75184 A1 | 12/2000 |
| WO | 02/100333 A2 | 12/2002 |
| WO | 03/023405 | 3/2003 |

OTHER PUBLICATIONS

Janelle Nunan et al., "*The C-terminal fragment of the Alzheimer's disease amyloid protein precursor is degraded by a proteasome-dependent mechanism distinct from γ-secretase*", Eur. J. Biochem., vol. 268, pp. 5329-5336 (2001).
Luisa Gregori et al., "*Ubiquitin-Mediated Degradative Pathway Degrades the Extra Cellular But Not the Intracellular Form of Amyloid β-Protein Precursor*", Biochemical and Biophysical Research Communications, vol. 203, No. 3, pp. 1731-1738 (1994).
Gennady P. Ilyin et al., "*cDNA Cloning and Expression Analysis of New Members of the Mamalian F-Box Protein Family*", Genomics, vol. 67, pp. 40-47 (2000).
Eric M. Blalock et al., "*Incipient Alzheimer's disease: Microarray correlation analyses reveal major transcriptional and tumor suppressor responses*", PNAS, vol. 101, No. 7, pp. 2173-2178 (2004).
Fred W. Van Leeuwen et al., "*Frameshift Mutants of β Amyloid Precursor Protein and Ubiquitin-B in Alzheimer's and Down Patients*", Science, vol. 279, pp. 242-247 (1998).
European Patent Search Report issued on Jun. 29, 2009 for the corresponding European Patent Application No. 06713546.
Nunan Janelle et al., "*Proteasome-mediated degradation of the C-terminus of the Alzheimer's Disease beta-amyloid protein precursor: effect of C-terminal truncation on production of beta-amyloid protein.*", Journal of Neuroscience Research, vol. 74, No. 3, Nov. 1, 2003, pp. 378-385, XP002532260.
Winston et al., "*A family of mammalian F-box proteins*", Current Biology, Current Science, GB, vol. 9, No. 20, Oct. 21, 1999, pp. 1180-1182, XP005106516.
De Vrij F M S et al., "*Protein quality control in Alzheimer's disease by the ubiquitin proteasome system*", Progress in Neurobiology, Pergamon Press, GB, vol. 74, No. 5, Dec. 1, 2004, pp. 249-270, XP004668681.

* cited by examiner

*Primary Examiner* — Daniel E Kolker
*Assistant Examiner* — Gregory S Emch
(74) *Attorney, Agent, or Firm* — Wenderoth, Lind & Ponack, L.L.P.

(57) ABSTRACT

A compound that promotes the ubiquitination of a protein comprising the same or substantially the same amino acid sequence as the amino acid sequence shown by SEQ ID NO:1, SEQ ID NO:2 or SEQ ID NO:3 or a partial peptide thereof or a salt thereof, or a salt thereof, a compound that promotes the degradation, by proteasome, of the protein or a partial peptide thereof or a salt thereof, or a salt thereof, and the like can be used as, for example, prophylactic/therapeutic agents for neurodegenerative disease. Also, a protein comprising the same or substantially the same amino acid sequence as the amino acid sequence shown by SEQ ID NO:1, SEQ ID NO:2 or SEQ ID NO:3 or a partial peptide thereof or a salt thereof and the like are useful for screening for a compound having prophylactic/therapeutic action on neurodegenerative disease and the like or a salt thereof.

3 Claims, No Drawings

SCREENING METHOD FOR AN AGENT FOR TREATMENT OF NEURODEGENERATIVE DISEASE

This application is a U.S. national stage of International Application No. PCT/JP2006/302404 filed Feb. 6, 2006.

TECHNICAL FIELD

The present invention relates to a prophylactic/therapeutic agent and diagnostic reagent for neurodegenerative disease, a screening therefor and the like.

BACKGROUND ART

Alzheimer's disease is representative of neurodegenerative diseases accompanied by progressive dementia and a loss of cognitive performance, for which no effective therapy has been found to date. Alzheimer's disease is of course one of the most important diseases in the present time of aging society, and development of a therapeutic drug therefor is of paramount importance in medical economics.

On the other hand, abnormal proteins produced due to various forms of external stress, including heat shock and glucose starvation, are known to undergo rapid degradation in vivo via the ubiquitine-proteasome pathway. Ubiquitin is joined to an abnormal protein formed in vivo by a complex enzyme system configured with ubiquitin activation enzyme (E1), ubiquitin binding enzyme (E2), and ubiquitin ligase (E3), and this is followed by repeats of the E1-E2-E3 cycle, whereby a polyubiquitin chain comprising a large number of ubiquitin molecules linked together on branches is formed. This polyubiquitin chain serves as a degradation signal for 26S proteasome, and the abnormal protein is rapidly destroyed.

In recent years, emphasis has been placed on the relationship between various neurodegenerative diseases, including Alzheimer's disease and Parkinson's disease, and abnormalities in the ubiquitine-proteasome pathway. For example, in Alzheimer's disease patients, expression of mutant ubiquitin was demonstrated (Science, Vol. 279, pp. 242-247, 1998), and it was reported that proteasome activity was inhibited by this mutant ubiquitin (Proc. Natl. Acad. Sci. USA, Vol. 97, pp. 9902-9906, 2000; J. Cell. Biol, Vol. 157, pp. 417-427, 2002). In autosomal recessive hereditary juvenile Parkinsonism (AR-JP), a hereditary form of Parkinson's disease, Parkin was identified as the etiologic gene (Nature, Vol. 392, pp. 605-608, 1998), and was reported to be a ubiquitin ligase involved in the protein degradation system (Nat. Genet, Vol. 25, pp. 302-305, 2000). Furthermore, as the substrate for Parkin, the Pael (Parkin associated endothelin receptor-like) receptor was identified (Cell, Vol. 105, pp. 891-902, 2001). This receptor is a kind of protein unlikely to form a higher-order structure; if the formation of the higher-order structure of this protein is incomplete, the protein will undergo quick degradation by the action of parkin. However, it has been reported that if this protein degradation system is suppressed due to any abnormality, the Pael receptor with an incompletely formed higher-order structure accumulates in the endoplasmic reticulum, and that cells die of endoplasmic reticulum stress caused by the accumulation.

A feature of the ubiquitin system resides in that ubiquitination occurs very specifically and timely. On the other hand, it is known that a vast number of target proteins are ubiquitinated in cells. Recently, it was found that E3 in the ubiquitine-proteasome pathway exhibits a great molecular diversity, and it was demonstrated that about 1,000 different kinds of E3 are encoded in the human genome. Hence, it was shown that the multiplicity of target proteins is coped with by this number of E3 (Igaku no Ayumi, Vol. 211, pp. 5-11, 2004). E3, among the three groups of enzymes involved in ubiquitination reactions, is a type of enzyme that interacts directly with substrate protein to determine substrate specificity. E3 can be classified into three major groups according to the domain serving as the center of activity: HECT type, RING type, and U-box type. The HECT type and U-box type function as E3 in the form of monomers, whereas the RING type functions in two ways: one functions as a monomer and one functions as a complex with a protein having a RING finger domain, such as Rbx1; the latter is called Cullin-based E3 because it contains a Cullin family protein as the scaffold protein. The SCF complex (S-phase kinase-associated protein 1A (Skp1)-Cullin1-Ring box 1 (Rbx1) complex), which is a kind of this complex, functions as E3 by forming a tetramer of the Skp1, Cullin1, Rbx1, and F-box proteins. Of these proteins, Skp1, Cullin1, and Rbx1 are invariable common components, whereas the F-box protein is a variable component; SCF type ubiquitin ligase is considered to promote the ubiquitination of specific substrate by exchanging F-box proteins, and to date at least 55 kinds of F-box protein have been identified. F-box proteins have an F-box domain for binding to the adapter molecule Skp1 and a domain for binding to substrate protein, and are classified into three types according to the kind of this domain for binding to substrate protein: (i) those having a WD40 repeat domain (Fbw family), (ii) those having a leucine-rich repeat (LRR) (Fbl family), and (iii) others (Fbx family). A kind of F-box protein is considered to bind to some substrate proteins, and to be involved in the ubiquitination of a particular substrate protein. There are some cases in which this binding requires a modification such as phosphorylation. The SCF complex is also diverse in that it is capable of ubiquitinating a very large number of substrate proteins by exchanging F-box proteins; other Cullin-based E3 is known to form a similar complex with the SCF complex, and to be involved in the ubiquitination of other substrate protein as a unique E3 functional molecule.

F-box and leucine rich repeat protein 2 (FBL2) is one of the constituents of the SCF complex, and functions as a F-box protein. FBL2 has been shown to be expressed specifically in the brain and testis (Genomics, Vol. 67, pp. 40-47, 2000), and it has further been reported that the expression of the gene for this protein decreases in the brains of Alzheimer's disease patients (Proc. Natl. Acad. Sci. USA, Vol. 101, pp. 2173-2178, 2004). Although FBL2 is considered to bind to a specific substrate in the leucine-rich repeat region at the C terminus to accentuate ubiquitination, no substrate that binds to FBL2 has been identified to date.

Described in Official Gazette for WO 03/023405 is a therapeutic or prophylactic method for neurodegenerative disease, particularly Alzheimer's disease, in a subject, comprising administering to the subject a therapeutically or prophylactically effective amount of a drug (drugs) that directly or indirectly influences the activity and/or level of (i) the gene that encodes the F-box leucine-rich repeat protein and/or (ii) the transcription product of the gene that encodes the F-box leucine-rich repeat protein and/or (iii) the translation product of the gene that encodes the F-box leucine-rich repeat protein, and/or (iv) a fragment, or derivative, or mutant of (i) to (iii).

Yippee-like 1 (YPEL1) was identified as a gene expressed in the craniofacial genesis stage of mouse viviparity (Genes Cells, Vol. 6, pp. 619-629, 2001), and it has been reported to date that YPEL 1 to 5 exist as genes of the same family (GENE, Vol. 340, pp. 31-43, 2004). Of the genes of the YPEL family, YPEL1 is expressed specifically in the testis and fetal brain, whereas YPEL 2 to 5 are expressed in multiple organs. Because the genes of the YPEL family are localized in the nucleus, particularly abundant in the centrosome, they are considered to be possibly involved in the cell division stage. However, there is only one report that transient expression of YPEL1 in fibroblasts like NIH3T3 cells causes a morphological change like epithelial cells, and no report is available on the function thereof.

DISCLOSURE OF THE INVENTION

There is a demand for a safe and excellent prophylactic/therapeutic agent for neurodegenerative disease.

To solve the above-described problems, and with the expectation that a target gene for drug discovery for neurodegenerative disease could be discovered from among the genes involved in the ubiquitine-proteasome pathway, the present inventors performed diligent investigations and found that FBL2, a kind of F-box protein, which is a constituent of the SCF complex, binds to amyloid precursor protein (APP) and the like, and that regulation of FBL2 expression influences the production of β amyloid (Aβ). The present inventors performed further investigations and developed the present invention.

Accordingly, the present invention relates to:

[1] A prophylactic/therapeutic agent for neurodegenerative disease, comprising a compound that promotes the ubiquitination of a protein comprising the same or substantially the same amino acid sequence as the amino acid sequence shown by SEQ ID NO:1, SEQ ID NO:2 or SEQ ID NO:3 or a partial peptide thereof or a salt thereof, or a salt thereof,

[1a] a prophylactic/therapeutic agent for diabetes mellitus, comprising a compound that promotes the ubiquitination of a protein comprising the same or substantially the same amino acid sequence as the amino acid sequence shown by SEQ ID NO:1, SEQ ID NO:2 or SEQ ID NO:3 or a partial peptide thereof or a salt thereof, or a salt thereof,

[2] a prophylactic/therapeutic agent for neurodegenerative disease, comprising a compound that promotes the degradation, by proteasome, of a protein comprising the same or substantially the same amino acid sequence as the amino acid sequence shown by SEQ ID NO:1, SEQ ID NO:2 or SEQ ID NO:3 or a partial peptide thereof or a salt thereof, or a salt thereof,

[3] the agent described in [1], [1a] or [2] above, wherein the compound is a compound that promotes the binding of a protein comprising a protein comprising the same or substantially the same amino acid sequence as the amino acid sequence shown by SEQ ID NO:23 or a partial peptide thereof or a salt thereof and a protein comprising the same or substantially the same amino acid sequence as the amino acid sequence shown by SEQ ID NO:1, SEQ ID NO:2 or SEQ ID NO:3 or a partial peptide thereof or a salt thereof,

[3a] a prophylactic/therapeutic agent for neurodegenerative disease, comprising a compound that promotes the binding of (i) a protein comprising a protein comprising the same or substantially the same amino acid sequence as the amino acid sequence shown by SEQ ID NO:23 or a partial peptide thereof or a salt thereof and (ii) a protein comprising the same or substantially the same amino acid sequence as the amino acid sequence shown by SEQ ID NO:1, SEQ ID NO:2 or SEQ ID NO:3 or a partial peptide thereof or a salt thereof, or a salt thereof,

[4] the agent described in [3] or [3a] above, wherein the protein comprising the protein comprising the same or substantially the same amino acid sequence as the amino acid sequence shown by SEQ ID NO:23 or a partial peptide thereof or a salt thereof is an SCF complex,

[5] the agent described in [1], [1a], or [2] above, wherein the compound is a compound that promotes the binding of a protein comprising the same or substantially the same amino acid sequence as the amino acid sequence shown by SEQ ID NO:23 or a partial peptide thereof or a salt thereof and a protein comprising the same or substantially the same amino acid sequence as the amino acid sequence shown by SEQ ID NO:1, SEQ ID NO:2 or SEQ ID NO:3 or a partial peptide thereof or a salt thereof,

[5a] a prophylactic/therapeutic agent for neurodegenerative disease, comprising a compound that promotes the binding of (i) a protein comprising the same or substantially the same amino acid sequence as the amino acid sequence shown by SEQ ID NO:23 or a partial peptide thereof or a salt thereof and (ii) a protein comprising the same or substantially the same amino acid sequence as the amino acid sequence shown by SEQ ID NO:1, SEQ ID NO:2 or SEQ ID NO:3 or a partial peptide thereof or a salt thereof, or a salt thereof,

[6] a prophylactic/therapeutic agent for neurodegenerative disease, comprising a compound that promotes the expression of a protein comprising the same or substantially the same amino acid sequence as the amino acid sequence shown by SEQ ID NO:23 or a partial peptide thereof or a salt thereof, or a salt thereof,

[7] a prophylactic/therapeutic agent for neurodegenerative disease, comprising a compound that promotes the expression of a polynucleotide that encodes the gene for a protein comprising the same or substantially the same amino acid sequence as the amino acid sequence shown by SEQ ID NO:23 or a partial peptide thereof, or a salt thereof,

[8] a screening method for a compound that promotes the ubiquitination of a protein comprising the same or substantially the same amino acid sequence as the amino acid sequence shown by SEQ ID NO:1, SEQ ID NO:2 or SEQ ID NO:3 or a partial peptide thereof or a salt thereof, or a salt thereof, comprising using the protein or a partial peptide thereof or a salt thereof,

[9] a screening method for a compound that promotes the degradation, by proteasome, of a protein comprising the same or substantially the same amino acid sequence as the amino acid sequence shown by SEQ ID NO:1, SEQ ID NO:2 or SEQ ID NO:3 or a partial peptide thereof or a salt thereof, or a salt thereof, comprising using the protein or a partial peptide thereof or a salt thereof,

[10] a screening method for a compound that promotes the binding of (i) a protein comprising a protein comprising the same or substantially the same amino acid sequence as the amino acid sequence shown by SEQ ID NO:23 or a partial peptide thereof or a salt thereof and (ii) a protein comprising the same or substantially the same amino acid sequence as the amino acid sequence shown by SEQ ID NO:1, SEQ ID NO:2 or SEQ ID NO:3 or a partial peptide thereof or a salt thereof, or a salt thereof, comprising using the protein (i) above and the protein (ii) above or a partial peptide thereof or a salt thereof,

[11] the screening method described in [10] above, wherein the protein comprising the protein comprising the same or substantially the same amino acid sequence as the amino acid sequence shown by SEQ ID NO:23 or a partial peptide thereof or a salt thereof is an SCF complex,

[12] a screening method for a compound that promotes the binding of (i) a protein comprising the same or substantially the same amino acid sequence as the amino acid sequence shown by SEQ ID NO:23 or a partial peptide thereof or a salt thereof and (ii) a protein comprising the same or substantially the same amino acid sequence as the amino acid sequence shown by SEQ ID NO:1, SEQ ID NO:2 or SEQ ID NO:3 or a partial peptide thereof or a salt thereof, or a salt thereof, comprising using the protein (i) above or a partial peptide thereof or a salt thereof and the protein (ii) above or a partial peptide thereof or a salt thereof,

[13] a screening kit for a compound that promotes the ubiquitination of a protein comprising the same or substantially the same amino acid sequence as the amino acid sequence shown by SEQ ID NO:1, SEQ ID NO:2 or SEQ ID NO:3 or a partial peptide thereof or a salt thereof, or a salt thereof, comprising the protein or a partial peptide thereof or a salt thereof,

[14] a screening kit for a compound that promotes the degradation, by proteasome, of a protein comprising the same or substantially the same amino acid sequence as the amino acid sequence shown by SEQ ID NO:1, SEQ ID NO:2 or SEQ ID NO:3 or a partial peptide thereof or a salt thereof, or a salt thereof, comprising the protein or a partial peptide thereof or a salt thereof,

[15] a screening kit for a compound that promotes the binding of (i) a protein comprising the same or substantially the same amino acid sequence as the amino acid sequence shown by SEQ ID NO:23 or a partial peptide thereof or a salt thereof and (ii) a protein comprising the same or substantially the same amino acid sequence as the amino acid sequence shown by SEQ ID NO:1, SEQ ID NO:2 or SEQ ID NO:3 or a partial peptide thereof or a salt thereof, or a salt thereof, comprising the protein (i) above or a partial peptide thereof or a salt thereof and the protein (ii) above or a partial peptide thereof or a salt thereof,

[16] a screening method for a compound that promotes the expression of a protein comprising the same or substantially the same amino acid sequence as the amino acid sequence shown by SEQ ID NO:23, or a salt thereof, comprising using the protein or a partial peptide thereof or a salt thereof,

[17] a screening method for a compound that promotes the expression of a polynucleotide that encodes the gene for a protein comprising the same or substantially the same amino acid sequence as the amino acid sequence shown by SEQ ID NO:23 or a partial peptide thereof, or a salt thereof, comprising using the polynucleotide,

[18] a screening method for a compound having prophylactic/therapeutic action on neurodegenerative disease or a salt thereof, comprising using a protein comprising the same or substantially the same amino acid sequence as the amino acid sequence shown by SEQ ID NO:23 or a partial peptide thereof or a salt thereof,

[19] a screening method for a compound having prophylactic/therapeutic action on neurodegenerative disease or a salt thereof, comprising using a polynucleotide that encodes the gene for a protein comprising the same or substantially the same amino acid sequence as the amino acid sequence shown by SEQ ID NO:23 or a partial peptide thereof,

[20] a prophylactic/therapeutic method for neurodegenerative disease, comprising promoting the ubiquitination of a protein comprising the same or substantially the same amino acid sequence as the amino acid sequence shown by SEQ ID NO:1, SEQ ID NO:2 or SEQ ID NO:3 or a partial peptide thereof or a salt thereof,

[20a] a prophylactic/therapeutic method for diabetes mellitus, comprising promoting the ubiquitination of a protein comprising the same or substantially the same amino acid sequence as the amino acid sequence shown by SEQ ID NO:1, SEQ ID NO:2 or SEQ ID NO:3 or a partial peptide thereof or a salt thereof,

[21] a prophylactic/therapeutic method for neurodegenerative disease, comprising administering, to a mammal, an effective amount of a compound that promotes the ubiquitination of a protein comprising the same or substantially the same amino acid sequence as the amino acid sequence shown by SEQ ID NO:1, SEQ ID NO:2 or SEQ ID NO:3 or a partial peptide thereof or a salt thereof, or a salt thereof,

[21a] a prophylactic/therapeutic method for diabetes mellitus, comprising administering, to a mammal, an effective amount of a compound that promotes the ubiquitination of a protein comprising the same or substantially the same amino acid sequence as the amino acid sequence shown by SEQ ID NO:1, SEQ ID NO:2 or SEQ ID NO:3 or a partial peptide thereof or a salt thereof, or a salt thereof,

[22] a use of a compound that promotes the ubiquitination of a protein comprising the same or substantially the same amino acid sequence as the amino acid sequence shown by SEQ ID NO:1, SEQ ID NO:2 or SEQ ID NO:3 or a partial peptide thereof or a salt thereof, or a salt thereof, for a prophylactic/therapeutic agent for neurodegenerative disease,

[22a] a use of a compound that promotes the ubiquitination of a protein comprising the same or substantially the same amino acid sequence as the amino acid sequence shown by SEQ ID NO:1, SEQ ID NO:2 or SEQ ID NO:3 or a partial peptide thereof or a salt thereof, or a salt thereof, for a prophylactic/therapeutic agent for diabetes mellitus,

[23] a prophylactic/therapeutic method for neurodegenerative disease, comprising promoting the degradation, by proteasome, of a protein comprising the same or substantially the same amino acid sequence as the amino acid sequence shown by SEQ ID NO:1, SEQ ID NO:2 or SEQ ID NO:3 or a partial peptide thereof or a salt thereof,

[24] a prophylactic/therapeutic method for neurodegenerative disease, comprising administering, to a mammal, an effective amount of a compound that promotes the degradation, by proteasome, of a protein comprising the same or substantially the same amino acid sequence as the amino acid sequence shown by SEQ ID NO:1, SEQ ID NO:2 or SEQ ID NO:3 or a partial peptide thereof or a salt thereof, or a salt thereof,

[25] a use of a compound that promotes the degradation, by proteasome, of a protein comprising the same or substantially the same amino acid sequence as the amino acid sequence shown by SEQ ID NO:1, SEQ ID NO:2 or SEQ ID NO:3 or a partial peptide thereof or a salt thereof, or a salt thereof, for a prophylactic/therapeutic agent for neurodegenerative disease,

[26] a prophylactic/therapeutic method for neurodegenerative disease, comprising promoting the expression of a protein comprising the same or substantially the same amino acid sequence as the amino acid sequence shown by SEQ ID NO:23 or a partial peptide thereof or a salt thereof,

[26a] a prophylactic/therapeutic method for neurodegenerative disease, comprising promoting the expression of a polynucleotide that encodes the gene for a protein comprising the same or substantially the same amino acid sequence as the amino acid sequence shown by SEQ ID NO:23 or a partial peptide thereof,

[27] a prophylactic/therapeutic method for neurodegenerative disease, comprising administering, to a mammal, an effective amount of a compound that promotes the expression of a protein comprising the same or substantially the same amino acid sequence as the amino acid sequence shown by SEQ ID NO:23 or a partial peptide thereof or a salt thereof, or a salt thereof,

[27a] a prophylactic/therapeutic method for neurodegenerative disease, comprising administering, to a mammal, an effective amount of a compound that promotes the expression of a polynucleotide that encodes the gene for a protein comprising the same or substantially the same amino acid sequence as the amino acid sequence shown by SEQ ID NO:23 or a partial peptide thereof, or a salt thereof,

[28] a use of a compound that promotes the expression of a protein comprising the same or substantially the same amino acid sequence as the amino acid sequence shown by SEQ ID NO:23 or a partial peptide thereof or a salt thereof, or a salt thereof, for a prophylactic/therapeutic agent for neurodegenerative disease,

[28a] a use of a compound that promotes the expression of a polynucleotide that encodes the gene for a protein comprising the same or substantially the same amino acid sequence as the amino acid sequence shown by SEQ ID NO:23 or a partial peptide thereof, or a salt thereof, for a prophylactic/therapeutic agent for neurodegenerative disease,

[29] a prophylactic/therapeutic method for neurodegenerative disease, comprising promoting the binding of (i) a protein comprising the same or substantially the same amino acid sequence as the amino acid sequence shown by SEQ ID NO:23 or a partial peptide thereof or a salt thereof and (ii) a protein comprising the same or substantially the same amino acid sequence as the amino acid sequence shown by SEQ ID NO:1, SEQ ID NO:2 or SEQ ID NO:3 or a partial peptide thereof or a salt thereof,

[29a] a prophylactic/therapeutic method for neurodegenerative disease, comprising promoting the binding of (i) a protein comprising a protein comprising the same or substantially the same amino acid sequence as the amino acid sequence shown by SEQ ID NO:23 or a partial peptide thereof or a salt thereof and (ii) a protein comprising the same or substantially the same amino acid sequence as the amino acid sequence shown by SEQ ID NO:1, SEQ ID NO:2 or SEQ ID NO:3 or a partial peptide thereof or a salt thereof,

[30] a prophylactic/therapeutic method for neurodegenerative disease, comprising administering, to a mammal, an effective amount of a compound that promotes the binding of (i) a protein comprising the same or substantially the same amino acid sequence as the amino acid sequence shown by SEQ ID NO:23 or a partial peptide thereof or a salt thereof and (ii) a protein comprising the same or substantially the same amino acid sequence as the amino acid sequence shown by SEQ ID NO:1, SEQ ID NO:2 or SEQ ID NO:3 or a partial peptide thereof or a salt thereof, or a salt thereof,

[30a] a prophylactic/therapeutic method for neurodegenerative disease, comprising administering, to a mammal, an effective amount of a compound that promotes the binding of (i) a protein comprising a protein comprising the same or substantially the same amino acid sequence as the amino acid sequence shown by SEQ ID NO:23 or a partial peptide thereof or a salt thereof and (ii) a protein comprising the same or substantially the same amino acid sequence as the amino acid sequence shown by SEQ ID NO:1, SEQ ID NO:2 or SEQ ID NO:3 or a partial peptide thereof or a salt thereof, or a salt thereof,

[31] a use of a compound that promotes the binding of (i) a protein comprising the same or substantially the same amino acid sequence as the amino acid sequence shown by SEQ ID NO:23 or a partial peptide thereof or a salt thereof and (ii) a protein comprising the same or substantially the same amino acid sequence as the amino acid sequence shown by SEQ ID NO:1, SEQ ID NO:2 or SEQ ID NO:3 or a partial peptide thereof or a salt thereof, or a salt thereof, for a prophylactic/therapeutic agent for neurodegenerative disease,

[31a] a use of a compound that promotes the binding of (i) a protein comprising a protein comprising the same or substantially the same amino acid sequence as the amino acid sequence shown by SEQ ID NO:23 or a partial peptide thereof or a salt thereof and (ii) a protein comprising the same or substantially the same amino acid sequence as the amino acid sequence shown by SEQ ID NO:1, SEQ ID NO:2 or SEQ ID NO:3 or a partial peptide thereof or a salt thereof, or a salt thereof, for a prophylactic/therapeutic agent for neurodegenerative disease, and the like.

BEST MODE FOR EMBODYING THE INVENTION

A protein comprising the same or substantially the same amino acid sequence as the amino acid sequence shown by SEQ ID NO:1, SEQ ID NO:2 or SEQ ID NO:3, used in the present invention (hereinafter also referred to as the protein of the present invention or the protein used in the present invention) may be a protein derived from any cells [for example, liver cells, splenocytes, nerve cells, glial cells, β cells of pancreas, bone marrow cells, mesangial cells, Langerhans' cells, epidermic cells, epithelial cells, goblet cells, endothelial cells, smooth muscle cells, fibroblasts, fibrocytes, myocytes, adipocytes, immune cells (e.g., macrophages, T cells, B cells, natural killer cells, mast cells, neutrophils, basophils, eosinophils, monocytes), megakaryocytes, synovial cells, chondrocytes, bone cells, osteoblasts, osteoclasts, mammary gland cells, hepatocytes or interstitial cells, or the corresponding precursor cells, stem cells, cancer cells and the like] of humans or other warm-blooded animals (for example, guinea pigs, rats, mice, chickens, rabbits, pigs, sheep, cattle, monkeys and the like), or from any tissues where such cells are present, for example, the brain or each region of the brain (e.g., olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, muscle, lung, gastrointestinal tract (e.g., large intestine, small intestine), blood vessel, heart, thymus, spleen, submandibular gland, peripheral blood, prostate, testis, ovary, placenta, uterus, bone, joint, skeletal muscle and the like, and may also be a synthetic protein.

As the protein comprising the same or substantially the same amino acid sequence as the amino acid sequence shown by SEQ ID NO:1, SEQ ID NO:2 or SEQ ID NO:3, an amino acid sequence showing a homology of about 50% or more, preferably about 60% or more, more preferably about 70% or more, still more preferably about 80% or more, particularly preferably about 90% or more, and most preferably about 95% or more, to the amino acid sequence shown by SEQ ID NO:1, SEQ ID NO:2 or SEQ ID NO:3 and the like can be mentioned.

The homology of an amino acid sequence can be calculated using the homology calculation algorithm NCBI BLAST (National Center for Biotechnology Information Basic Local Alignment Search Tool).

As the protein comprising the same or substantially the same amino acid sequence as the amino acid sequence shown by SEQ ID NO:1, SEQ ID NO:2 or SEQ ID NO:3, for example, a protein comprising substantially the same amino acid sequence as the aforementioned amino acid sequence shown by SEQ ID NO:1, SEQ ID NO:2 or SEQ ID NO:3, and having substantially the same quality of activity as a protein comprising the amino acid sequence shown by SEQ ID NO:1, SEQ ID NO:2 or SEQ ID NO:3 and the like are preferable.

As examples of substantially the same quality of activity, action to bind to the SCF complex (preferably FBL2) and the like can be mentioned. "Substantially the same quality"

means that the activities are qualitatively (e.g., physiologically or pharmacologically) equivalent to each other. Therefore, it is preferable that the above-described activities be equivalent to each other (for example, about 0.01 to 100 times, preferably about 0.1 to 10 times, more preferably about 0.5 to 2 times), but the quantitative factors of these activities, such as the extent of activity and the molecular weight of the protein, may be different.

A measurement of the above-described binding action can be performed by, for example, measuring the binding affinity of the protein of the present invention and the SCF complex (preferably FBL2).

Specifically, for example, by measuring surface plasmon resonance (SPR) using the Biacore apparatus (Biacore K.K.), an intermolecular interaction is analyzed. SPR is a technology for measuring the intensity, speed, and selectivity of molecular binding based on an integration of the three technologies of sensor chip, micro-flow path system, and SPR detection system; the Biacore apparatus enables monitoring of interactions between a plurality of molecules on real-time basis without using a marker.

For example, in measuring the binding affinity of the protein of the present invention for the SCF complex, the SCF complex is immobilized on the surface of a sensor chip, and the protein of the present invention is added thereto. Because the state of the interaction between these proteins can be examined on real-time basis using sensorgrams, the affinity and the coefficient of dissociation from the SCF complex are measured by comparing the binding and dissociation reaction curves obtained.

Examples of the protein of the present invention also include what are called muteins of proteins comprising (i) an amino acid sequence having one or two or more amino acids (for example, about 1 to 100, preferably about 1 to 30, more preferably about 1 to 10, and still more preferably several (1 to 5) amino acids) deleted from the amino acid sequence shown by SEQ ID NO:1, SEQ ID NO:2 or SEQ ID NO:3, (ii) an amino acid sequence having one or two or more amino acids (for example, about 1 to 100, preferably about 1 to 30, more preferably about 1 to 10, and still more preferably several (1 to 5) amino acids) added to the amino acid sequence shown by SEQ ID NO:1, SEQ ID NO:2 or SEQ ID NO:3, (iii) an amino acid sequence having one or two or more amino acids (for example, about 1 to 100, preferably about 1 to 30, more preferably about 1 to 10, and still more preferably several (1 to 5) amino acids) inserted in the amino acid sequence shown by SEQ ID NO:1, SEQ ID NO:2 or SEQ ID NO:3, (iv) an amino acid sequence having one or two or more amino acids (for example, about 1 to 100, preferably about 1 to 30, more preferably about 1 to 10, and still more preferably several (1 to 5) amino acids) substituted by other amino acids in the amino acid sequence shown by SEQ ID NO:1, SEQ ID NO:2 or SEQ ID NO:3, or (v) an amino acid sequence comprising a combination thereof, and the like.

When an amino acid sequence is inserted, deleted or substituted as described above, the position of the insertion, deletion or substitution is not subject to limitation.

For the proteins in the present description, the left end indicates the N terminus (amino terminus) and the right end indicates the C-terminus (carboxyl terminus), according to the common practice of peptide designation. For the protein of the present invention, including proteins comprising the amino acid sequence shown by SEQ ID NO:1, the C-terminus may be a carboxyl group (—COOH), a carboxylate (—COO$^-$), an amide (—CONH$_2$) or an ester (—COOR).

Here, as R in the ester, a $C_{1-6}$ alkyl group, for example, methyl, ethyl, n-propyl, isopropyl, and n-butyl; a $C_{3-8}$ cycloalkyl group, for example, cyclopentyl and cyclohexyl; a $C_{6-12}$ aryl group, for example, phenyl and α-naphthyl; a phenyl-$C_{1-2}$ alkyl group, for example, benzyl and phenethyl; a $C_{7-14}$ aralkyl group such as an α-naphthyl-$C_{1-2}$ alkyl group such as α-naphthylmethyl; a pivaloyloxymethyl group; and the like are used.

When the protein of the present invention has a carboxyl group (or a carboxylate) at a position other than the C terminus, a protein wherein the carboxyl group is amidated or esterified is also included in the protein of the present invention. In this case, as the ester, the above-described ester at the C terminal, and the like, for example, are used.

Furthermore, the protein of the present invention also includes those having the amino group of the amino acid residue (e.g., methionine residue) at the N-terminus protected by a protecting group (for example, $C_{1-6}$ acyl groups such as $C_{1-6}$ alkanoyls such as formyl group and acetyl group, and the like); those having the glutamine residue resulting from cleavage on the N-terminus side in vivo pyroglutamated; those having a substituent (for example, —OH, —SH, amino group, imidazole group, indole group, guanidino group and the like) on the side chain of an amino acid in the molecule protected by an appropriate protecting group (for example, $C_{1-6}$ acyl groups such as $C_{1-6}$ alkanoyl groups such as formyl group and acetyl group, and the like), or complex protein having a sugar chain bound thereto, such as what is called a glycopeptide, and the like.

As specific examples of the protein of the present invention, for example, a protein comprising the amino acid sequence shown by SEQ ID NO:1, a protein comprising the amino acid sequence shown by SEQ ID NO:2, a protein comprising the amino acid sequence shown by SEQ ID NO:3 and the like can be mentioned.

The partial peptide of the protein of the present invention may be any partial peptide of the above-described protein of the present invention, preferably one having substantially the same quality of property as the above-described protein of the present invention. For example, a peptide having at least 20 or more, preferably 50 or more, more preferably 70 or more, still more preferably 100 or more, most preferably 200 or more, amino acids of the amino acid sequence that constitutes the protein of the present invention, and the like are used.

A partial peptide used in the present invention may have one or two or more amino acids (preferably about 1 to 10, more preferably several (1 to 5) amino acids) deleted from the amino acid sequence thereof, or have one or two or more amino acids (preferably about 1 to 20, more preferably about 1 to 10, and still more preferably several (1 to 5) amino acids) added to the amino acid sequence thereof, or have one or two or more amino acids (preferably about 1 to 20, more preferably about 1 to 10, and still more preferably several (1 to 5) amino acids) inserted in the amino acid sequence thereof, or have one or two or more amino acids (preferably about 1 to 10, more preferably several, and still more preferably about 1 to 5 amino acids) substituted by other amino acids in the amino acid sequence thereof.

Also, for the partial peptide used in the present invention, the C-terminus may be any of a carboxyl group (—COOH), a carboxylate (—COO$^-$), an amide (—CONH$_2$) or an ester (—COOR).

Furthermore, the partial peptides used in the present invention, like the aforementioned proteins used in the present invention, also include those having a carboxyl group (or a carboxylate) at a position other than the C-terminus, those having the amino group of an amino acid residue (e.g., methionine residue) at the N-terminus protected by a protecting group; those having the glutamine residue resulting from cleavage on the N-terminus side in vivo pyroglutamated; those having a substituent on the side chain of an amino acid in the molecule protected by an appropriate protecting group, or complex peptides having a sugar chain bound thereto, such as what is called a glycopeptide, and the like.

A partial peptide used in the present invention can also be used as an antigen for generating an antibody.

As the salt of the protein or partial peptide of the present invention, salts with physiologically acceptable acids (e.g., inorganic acids, organic acids), bases (e.g., alkali metal salts) and the like are used, and physiologically acceptable acid addition salts are particularly preferable. As such a salt, for example, salts with inorganic acids (for example, hydrochloric acid, phosphoric acid, hydrobromic acid, sulfuric acid) or salts with organic acids (for example, acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like can be mentioned.

The protein of the present invention or a partial peptide thereof or a salt thereof can be produced from the above-described cells or tissues of human or other warm-blooded animals by a method of protein purification known per se, and can also be produced by culturing a transformant comprising a DNA that encodes the protein. The protein of the present invention or a partial peptide thereof or a salt thereof can also be produced in accordance with the peptide synthesis method described below.

When the protein of the present invention or a partial peptide thereof or a salt thereof is produced from a tissue or cells of a human or another mammal, it can be purified and isolated by homogenizing the tissue or cells of the human or mammal, then performing extraction with acid and the like, and subjecting the extract to a combination of chromatographies such as reversed phase chromatography and ion exchange chromatography.

For the synthesis of the protein of the present invention or a partial peptide or a salt thereof, or an amide thereof, an ordinary commercially available resin for protein synthesis can be used. As examples of such resins, chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenylacetamidomethyl resin, polyacrylamide resin, 4-(2',4'-dimethoxyphenyl-hydroxymethyl)phenoxy resin, 4-(2',4'-dimethoxyphenyl-Fmoc-aminoethyl)phenoxy resin and the like can be mentioned. Using such a resin, an amino acid having an appropriately protected α-amino group and side chain functional group is condensed on the resin in accordance with the sequence of the desired protein according to one of various methods of condensation known per se. At the end of the reaction, the protein or partial peptide is cleaved from the resin and at the same time various protecting groups are removed, and a reaction to form an intramolecular disulfide bond is carried out in a highly diluted solution to obtain the desired protein or partial peptide or an amide thereof.

For the above-described condensation of protected amino acids, various activation reagents which can be used for protein synthesis can be used, and a carbodiimide is preferably used. As the carbodiimide, DCC, N,N'-diisopropylcarbodiimide, N-ethyl-N'-(3-dimethylaminopropyl)carbodiimide and the like are used. For the activation using these carbodiimides, the protected amino acid, along with a racemization-suppressing additive (for example, HOBt, HOOBt), may be added directly to the resin, or the protected amino acid may be activated in advance as a symmetric acid anhydride or HOBt ester or HOOBt ester and then added to the resin.

Solvents used for the activation of protected amino acids and condensation thereof with a resin can be appropriately selected from among solvents known to be usable for protein condensation reactions. As examples of useful solvents, acid amides such as N,N-dimethylformamide, N,N-dimethylacetamide and N-methylpyrrolidone; halogenated hydrocarbons such as methylene chloride and chloroform; alcohols such as trifluoroethanol; sulfoxides such as dimethyl sulfoxide; ethers such as pyridine, dioxane and tetrahydrofuran; nitriles such as acetonitrile and propionitrile; esters such as methyl acetate and ethyl acetate; suitable mixtures thereof; and the like can be mentioned. Reaction temperature is appropriately selected from the range known to be usable for protein binding reactions, and is normally selected from the range of about −20° C. to 50° C. An activated amino acid derivative is normally used from 1.5 to 4 times in excess. A test using the ninhydrin reaction reveals that when the condensation is insufficient, sufficient condensation can be performed by repeating the condensation reaction without elimination of protecting groups. If the condensation is insufficient even though the reaction is repeated, unreacted amino acids may be acetylated using acetic anhydride or acetylimidazole to prevent the subsequent reaction from being influenced.

As examples of the protecting group for an amino group of the starting material, Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulfenyl, diphenylphosphinothioyl, Fmoc and the like can be used.

A carboxyl group can be protected by, for example, alkyl esterification (for example, linear, branched or cyclic alkyl esterification with methyl, ethyl, propyl, butyl, t-butyl, cyclopentyl, cyclohexyl, cycloheptyl, cyclooctyl, 2-adamantyl and the like), aralkyl esterification (for example, benzyl esterification, 4-nitrobenzyl esterification, 4-methoxybenzyl esterification, 4-chlorobenzyl esterification, benzhydryl esterification), phenacyl esterification, benzyloxycarbonyl hydrazidation, t-butoxycarbonyl hydrazidation, trityl hydrazidation and the like.

The hydroxyl group of serine can be protected by, for example, esterification or etherification. As examples of a group suitable for this esterification, lower ($C_{1-6}$) alkanoyl groups such as an acetyl group, aroyl groups such as a benzoyl group, and groups derived from carbonic acid such as a benzyloxycarbonyl group and an ethoxycarbonyl group, and the like are used. As examples of a group suitable for etherification, a benzyl group, a tetrahydropyranyl group, a t-butyl group and the like can be mentioned.

As examples of the protecting group for the phenolic hydroxyl group of tyrosine, Bzl, $C_{1-2}$-Bzl, 2-nitrobenzyl, Br-Z, t-butyl and the like can be used.

As examples of the protecting group for the imidazole of histidine, Tos, 4-methoxy-2,3,6-trimethylbenzenesulfonyl, DNP, benzyloxymethyl, Bum, Boc, Trt, Fmoc and the like are used.

As examples of those obtained by activation of the carboxyl group in the starting material, a corresponding acid anhydride, an azide, an activated ester [an ester with an alcohol (for example, pentachlorophenol, 2,4,5-trichlorophenol, 2,4-dinitrophenol, cyanomethyl alcohol, p-nitrophenol, HONB, N-hydroxysuccimide, N-hydroxyphthalimide, or HOBt)] and the like are used. As examples of those obtained by activation of the amino group in the starting material, a corresponding phosphoric amide is used.

As examples of the method of removing (eliminating) a protecting group, catalytic reduction in a hydrogen stream in the presence of a catalyst such as Pd-black or Pd-carbon; acid treatment by means of anhydrous hydrogen fluoride, methanesulfonic acid, trifluoromethanesulfonic acid, trifluoroacetic acid or a mixed solution thereof; base treatment by means of diisopropylethylamine, triethylamine, piperidine, piperazine or the like; and reduction with sodium in liquid ammonia, and the like are used. The elimination reaction by the above-described acid treatment is generally carried out at a temperature of about −20° C. to 40° C.; the acid treatment is efficiently performed by adding a cation scavenger, for example, anisole, phenol, thioanisole, m-cresol, p-cresol, dimethylsulfide, 1,4-butanedithiol and 1,2-ethanedithiol. Also, a 2,4-dinitrophenyl group used as a protecting group for the imidazole of histidine is removed by thiophenol treatment; a formyl group used as a protecting group for the indole of tryptophan is removed by acid treatment in the presence of 1,2-ethanedithiol, 1,4-butanedithiol or the like, as well as by alkali treatment with a dilute sodium hydroxide solution, dilute ammonia or the like.

A protecting method and a protecting group for a functional group that should not be involved in the reaction of raw materials, a method of eliminating the protecting group, a method of activating a functional group involved in the reaction, and the like can be appropriately selected from among commonly known groups or publicly known means.

In another method of preparing an amide of a protein or a partial peptide, for example, the α-carboxyl group of the carboxy-terminal amino acid is first amidated and hence protected, and a peptide (protein) chain is elongated to a desired chain length toward the amino group side, thereafter a protein or partial peptide having the protecting group for the N-terminal α-amino group of the peptide chain only removed and a protein or partial peptide having the protecting group for the C-terminal carboxyl group only removed are prepared, and these proteins or peptides are condensed in a mixed solvent described above. For details about the condensation reaction, the same as those described above applies. After the protected protein or peptide obtained by the condensation is purified, all protecting groups can be removed by the above-described method to yield a desired crude protein or peptide. By purifying this crude protein or peptide using various publicly known means of purification, and freeze-drying the main fraction, a desired amide of the protein or peptide can be prepared.

In order to obtain an ester of a protein or peptide, a desired ester of the protein or peptide can be prepared by, for example, condensing the α-carboxyl group of the carboxy-terminal amino acid with a desired alcohol to yield an amino acid ester, and then treating the ester in the same manner as with an amide of the protein or peptide.

The partial peptide or salt thereof used in the present invention can be produced according to a method of peptide synthesis known per se, or by cleaving the protein used in the present invention with an appropriate peptidase. The method of peptide synthesis may be any of, for example, a solid phase synthesis process and a liquid phase synthesis process. That is, a desired peptide can be produced by condensing a partial peptide or amino acid capable of constituting a partial peptide used in the present invention with the remaining portion, and eliminating any protecting group the resultant product may have.

As examples of commonly known methods of condensation and elimination of the protecting group, methods described in [i] to [v] below can be mentioned.

[i] M. Bodanszky and M. A. Ondetti: Peptide Synthesis, Interscience Publishers, New York (1966)
[ii] Schroeder and Luebke: The Peptide, Academic Press, New York (1965)
[iii] Nobuo Izumiya et al.: Peptide Gosei-no-Kiso to Jikken, published by Maruzen Co. (1975)
[iv] Haruaki Yajima and Shunpei Sakakibara: Seikagaku Jikken Koza 1, Tanpakushitsu no Kagaku IV, 205 (1977)
[v] Haruaki Yajima, ed.: Zoku Iyakuhin no Kaihatsu, Vol. 14, Peptide Synthesis, published by Hirokawa Shoten After the reaction, a partial peptide used in the present invention can be purified and isolated by a combination of ordinary methods of purification, for example, solvent extraction, distillation, column chromatography, liquid chromatography, recrystallization and the like. When the partial peptide obtained by the above-described method is a free form, the free form can be converted to an appropriate salt by a commonly known method or a method based thereon; conversely, when the partial peptide is obtained in the form of a salt, the salt can be converted to a free form or another salt by a commonly known method or a method based thereon.

The polynucleotide that encodes the protein of the present invention may be any one comprising the above-described base sequence that encodes the protein of the present invention. The polynucleotide is preferably a DNA. The DNA may be any of a genomic DNA, a genomic DNA library, a cDNA derived from the above-described cell or tissue, a cDNA library derived from the above-described cell or tissue, and a synthetic DNA.

The vector used for the library may be any of bacteriophage, plasmid, cosmid, phagemid and the like. The vector can also be directly amplified using a total RNA or mRNA fraction prepared from the above-described cell/tissue, by Reverse Transcriptase Polymerase Chain Reaction (hereinafter abbreviated as the RT-PCR method).

The DNA that encodes a protein used in the present invention may, for example, be any one of a DNA comprising the base sequence shown by SEQ ID NO:20, SEQ ID NO:21 or SEQ ID NO:22, or a DNA comprising a base sequence that hybridizes with the base sequence shown by SEQ ID NO:20, SEQ ID NO:21 or SEQ ID NO:22 under high stringent conditions, and having substantially the same quality of property as the above-described protein comprising the amino acid sequence shown by SEQ ID NO:1, SEQ ID NO:2 or SEQ ID NO:3.

As the DNA capable of hybridizing to the base sequence shown by SEQ ID NO:20, SEQ ID NO:21 or SEQ ID NO:22 under high stringent conditions, for example, a DNA comprising a base sequence showing a homology of about 50% or more, preferably about 60% or more, more preferably about 70% or more, still more preferably about 80% or more, particularly preferably about 90% or more, and most preferably about 95% or more, to the base sequence shown by SEQ ID NO:20, SEQ ID NO:21 or SEQ ID NO:22 and the like are used.

The homology of a base sequence can be calculated using the homology calculation algorithm NCBI BLAST (National Center for Biotechnology Information Basic Local Alignment Search Tool) under the following conditions (expectancy=10; gap allowed; filtering=ON; match score=1; mismatch score=−3).

Hybridization can be performed according to a method known per se or a method based thereon, for example, a method described in Molecular Cloning, 2nd (J. Sambrook et al., Cold Spring Harbor Lab. Press, 1989) and the like. When a commercially available library is used, hybridization can be performed according to the method described in the instruction manual attached thereto. More preferably, hybridization can be performed under high stringent conditions.

High-stringent conditions refer to, for example, conditions involving a sodium concentration of about 19 to 40 mM, preferably about 19 to 20 mM, and a temperature of about 50 to 70° C., preferably about 60 to 65° C. In particular, a case wherein the sodium concentration is about 19 mM and the temperature is about 65° C. is most preferable.

More specifically, as the DNA that encodes a protein comprising the amino acid sequence shown by SEQ ID NO:1, a DNA comprising the base sequence shown by SEQ ID NO:20 and the like are used; as the DNA that encodes a protein comprising the amino acid sequence shown by SEQ ID NO:2, a DNA comprising the base sequence shown by SEQ ID NO:21 and the like are used; as the DNA that encodes a protein comprising the amino acid sequence shown by SEQ ID NO:3, a DNA comprising the base sequence shown by SEQ ID NO:22 and the like are used.

A polynucleotide (e.g., DNA) that encodes a partial peptide used in the present invention may be any one comprising the above-described base sequence that encodes a partial peptide used in the present invention. The polynucleotide may be any of a genomic DNA, a genomic DNA library, a cDNA derived from the above-described cell or tissue, a cDNA library derived from the above-described cell or tissue, and a synthetic DNA.

As the DNA that encodes a partial peptide used in the present invention, for example, a DNA having a portion of a DNA comprising the base sequence shown by SEQ ID NO:20, SEQ ID NO:21 or SEQ ID NO:22, or a DNA comprising a portion of a DNA that encodes a protein comprising a base sequence that hybridizes to the base sequence shown by SEQ ID NO:20, SEQ ID NO:21 or SEQ ID NO:22 under high stringent conditions, and having substantially the same quality of activity as the protein of the present invention, and the like are used.

The DNA capable of hybridizing to the base sequence shown by SEQ ID NO:20, SEQ ID NO:21 or SEQ ID NO:22 has the same definition as that described above.

The method of hybridization and high stringent conditions used are the same as those described above.

As a means of cloning a DNA that completely encodes a protein or partial peptide used in the present invention (in the explanation of the cloning and expression of DNAs that encode them, these are sometimes simply abbreviated as the protein of the present invention), the DNA can be amplified by a PCR method using a synthetic DNA primer having a portion of a base sequence that encodes the protein of the present invention, or the DNA incorporated in an appropriate vector can be selected by hybridization with one labeled using a DNA fragment or synthetic DNA that encodes a portion or the entire region of the protein of the present invention. Hybridization can be performed according to, for example, a method described in Molecular Cloning, 2nd (J. Sambrook et al., Cold Spring Harbor Lab. Press, 1989) and the like. When a commercially available library is used, hybridization can be performed according to the method described in the instruction manual attached thereto.

The base sequence of DNA can be converted according to a method known per se, such as the ODA-LA PCR method, the Gapped duplex method, or the Kunkel method, or a method based thereon, using PCR, a commonly known kit, for example, Mutan™-super Express Km (Takara Shuzo Co., Ltd.), Mutan™-K (Takara Shuzo Co., Ltd.) and the like.

The cloned protein-encoding DNA can be used as is, or after digestion with a restriction endonuclease or addition of a linker as desired, depending on the purpose of its use. The DNA may have the translation initiation codon ATG at the 5' end thereof, and the translation stop codon TAA, TGA or TAG at the 3' end thereof. These translation initiation codons and translation stop codons can be added using an appropriate synthetic DNA adapter.

An expression vector for the protein of the present invention can be produced by, for example, (i) cutting out a desired DNA fragment from a DNA that encodes the protein of the present invention, and (ii) joining the DNA fragment downstream of a promoter in an appropriate expression vector.

As the vector, plasmids derived from *Escherichia coli* (e.g., pBR322, pBR325, pUC12, pUC13); plasmids derived from *Bacillus subtilis* (e.g., pUB110, pTP5, pC194); plasmids derived from yeast (e.g., pSH19, pSH15); bacteriophages such as λ phage; animal viruses such as retrovirus, vaccinia virus and baculovirus; pA1-11, pXT1, pRc/CMV, pRc/RSV, pcDNAI/Neo, and the like are used.

The promoter used in the present invention may be any promoter, as long as it is appropriate for the host used to express the gene. For example, when an animal cell is used as the host, the SRα promoter, the SV40 promoter, the LTR promoter, the CMV promoter, the HSV-TK promoter and the like can be mentioned.

Of these promoters, the CMV (cytomegalovirus) promoter, the SRα promoter and the like are preferably used. When the host is a bacterium of the genus *Escherichia*, the trp promoter, the lac promoter, the recA promoter, the λ$P_L$ promoter, the lpp promoter, the T7 promoter and the like are preferred; when the host is a bacterium of the genus *Bacillus*, the SPO1 promoter, the SPO2 promoter, the penP promoter and the like are preferred; when the host is yeast, the PHO5 promoter, the PGK promoter, the GAP promoter, the ADH promoter and the like are preferred. When the host is an insect cell, the polyhedrin prompter, the P10 promoter and the like are preferred.

In addition to those described above, the expression vector may comprise an enhancer, a splicing signal, a polyA addition signal, a selection marker, a SV40 replication origin (hereinafter sometimes abbreviated as SV40ori) and the like as required. As examples of the selection marker, the dihydrofolate reductase (hereinafter also abbreviated as dhfr) gene [methotrexate (MTX) resistance], the ampicillin resistance gene (hereinafter also abbreviated as Amp$^r$), the neomycin resistance gene (hereinafter also abbreviated as Neo$^r$, G418 resistance) and the like can be mentioned. In particular, when a Chinese hamster cell lacking the dhfr gene is used in combination with the dhfr gene as the selection marker, a target gene can also be selected using a thymidine-free medium.

Also, as required, a signal sequence appropriate for the host is added to the N-terminal side of the protein of the present invention. Useful signal sequences include a PhoA signal sequence, an OmpA signal sequence and the like when the host is a bacterium of the genus *Escherichia*; an α-amylase signal sequence, a subtilisin signal sequence and the like when the host is a bacterium of the genus *Bacillus*; an MFα signal sequence, an SUC2 signal sequence and the like when the host is yeast; and an insulin signal sequence, an α-interferon signal sequence, an antibody molecule signal sequence and the like when the host is an animal cell.

Using the thus-constructed vector comprising a DNA that encodes the protein of the present invention, a transformant can be produced.

As the host, for example, a bacterium of the genus *Escherichia*, a bacterium of the genus *Bacillus*, yeast, an insect cell, an insect, an animal cell and the like are used.

As the bacterium of the genus *Escherichia* include, for example, *Escherichia coli* K12-DH1 [Proc. Natl. Acad. Sci. USA, Vol. 60, 160 (1968)], JM103 [Nucleic Acids Research, Vol. 9, 309 (1981)], JA221 [Journal of Molecular Biology, Vol. 120, 517 (1978)], HB101 [Journal of Molecular Biology, Vol. 41, 459 (1969)], C600 [Genetics, Vol. 39, 440 (1954)] and the like are used.

As the bacterium of the genus *Bacillus* include, for example, *Bacillus subtilis* MI114 [Gene, Vol. 24, 255 (1983)], 207-21 [Journal of Biochemistry, Vol. 95, 87 (1984)] and the like are used.

As the yeast, for example, *Saccharomyces cerevisiae* AH22, AH22R⁻, NA87-11A, DKD-5D, 20B-12, *Schizosaccharomyces pombe* NCYC1913, NCYC2036, *Pichia pastoris* KM71 and the like are used.

As the insect cell, for example, *Spodoptera frugiperda* cell (Sf cell), MG1 cell derived from the mid-intestine of *Trichoplusia ni*, High Five™ cell derived from an egg of *Trichoplusia ni*, cell derived from *Mamestra brassicae*, cell derived from *Estigmena acrea*, and the like are used when the virus is AcNPV. When the virus is BmNPV, *Bombyx mori* N cell (BmN cell) and the like are used. As the Sf cell, for example, the Sf9 cell (ATCC CRL1711), the Sf21 cell (both in Vaughn, J. L. et al., In Vivo, 13, 213-217 (1977) and the like are used.

As the insect, for example, a larva of *Bombyx mori* (Maeda et al., Nature, Vol. 315, 592 (1985)) and the like are used.

As the animal cell, for example, monkey cell COS-7, Vero, Chinese hamster cell CHO (hereinafter abbreviated as CHO cell), Chinese hamster cell lacking the dhfr gene CHO (hereinafter abbreviated as CHO(dhfr⁻) cell), mouse L cell, mouse AtT-20, mouse myeloma cell, mouse ATDC5 cell, rat GH3, human FL cell and the like are used.

A bacterium of the genus *Escherichia* can be transformed, for example, in accordance with a method described in Proc. Natl. Acad. Sci. U.S.A., Vol. 69, 2110 (1972), Gene, Vol. 17, 107 (1982) and the like.

A bacterium of the genus *Bacillus* can be transformed, for example, according to a method described in Molecular & General Genetics, Vol. 168, 111 (1979) and the like.

Yeast can be transformed, for example, in accordance with a method described in Methods in Enzymology, Vol. 194, 182-187 (1991), Proc. Natl. Acad. Sci. USA, Vol. 75, 1929 (1978) and the like.

An insect cell or insect can be transformed, for example, according to a method described in Bio/Technology, 6, 47-55 (1988) and the like.

An animal cell can be transformed, for example, in accordance with a method described in Saibo Kogaku (Cell Engineering), extra issue 8, Shin Saibo Kogaku Jikken Protocol (New Cell Engineering Experimental Protocol), 263-267 (1995), published by Shujunsha, or Virology, Vol. 52, 456 (1973).

Thus, a transformant transformed with an expression vector comprising a DNA that encodes the protein can be obtained.

When a transformant whose host is a bacterium of the genus *Escherichia* or a bacterium of the genus *Bacillus* is cultured, the culture medium used is preferably a liquid medium, in which a carbon source, a nitrogen source, an inorganic substance and others necessary for the growth of the transformant are contained. As examples of the carbon source, glucose, dextrin, soluble starch, sucrose and the like can be mentioned; as examples of the nitrogen source, inorganic or organic substances such as an ammonium salt, a nitrate salt, corn steep liquor, peptone, casein, meat extract, soybean cake, and potato extract can be mentioned; as examples of the inorganic substance, calcium chloride, sodium dihydrogen phosphate, magnesium chloride and the like can be mentioned. In addition, yeast extract, vitamins, a growth promoting factor and the like may be added. The pH of the medium is desirably about 5 to 8.

As an example of the medium used to culture a bacterium of the genus *Escherichia*, a M9 medium supplemented with glucose and a casamino acid (Miller, Journal of Experiments in Molecular Genetics, 431-433, Cold Spring Harbor Laboratory, New York, 1972) is preferable. As required, in order to increase promoter efficiency, a chemical agent, for example, 3β-indolylacrylic acid, may be added to the medium.

When the host is a bacterium of the genus *Escherichia*, cultivation is normally performed at about 15 to 43° C. for about 3 to 24 hours, and the culture may be aerated or agitated as necessary.

When the host is a bacterium of the genus *Bacillus*, cultivation is normally performed at about 30 to 40° C. for about 6 to 24 hours, and the culture may be aerated or agitated as necessary.

When a transformant whose host is yeast is cultured, as examples of the medium, Burkholder's minimal medium [Bostian, K. L. et al., Proc. Natl. Acad. Sci. USA, Vol. 77, 4505 (1980)] and an SD medium supplemented with 0.5% casamino acid [Bitter, G. A. et al., Proc. Natl. Acad. Sci. USA, Vol. 81, 5330 (1984)] can be mentioned. The pH of the medium is preferably adjusted to about 5 to 8. Cultivation is normally performed at about 20° C. to 35° C. for about 24 to 72 hours, and the culture may be aerated or agitated as necessary.

When a transformant whose host is an insect cell or insect is cultured, as the medium, Grace's Insect Medium (Grace, T. C. C., Nature, 195, 788 (1962)) supplemented with inactivated 10% bovine serum and other additives as appropriate and the like are used. The pH of the medium is preferably adjusted to about 6.2 to 6.4. Cultivation is normally performed at about 27° C. for about 3 to 5 days, and the culture may be aerated or agitated as necessary.

When a transformant whose host is an animal cell is cultured, as examples of the medium, an MEM medium comprising about 5 to 20% fetal calf serum [Science, Vol. 122, 501 (1952)], DMEM medium [Virology, Vol. 8, 396 (1959)), RPMI1640 medium [The Journal of the American Medical Association Vol. 199, 519 (1967)], 199 medium [Proceeding of the Society for the Biological Medicine, Vol. 73, 1 (1950)] and the like are used. The pH is preferably about 6 to 8. Cultivation is normally performed at about 30° C. to 40° C. for about 15 to 60 hours, and the culture may be aerated or agitated as necessary.

Thus, the protein of the present invention can be produced in the cells, in the cell membrane or out of the cells of the transformant.

Separation and purification of the protein of the present invention from the above-described culture can be performed by, for example, the method described below.

When the protein of the present invention is extracted from a cultured bacterium or cells, a method is used as appropriate wherein the bacterium or cells are collected by a commonly known means after cultivation, suspended in an appropriate buffer solution, and disrupted by means of sonication, lysozyme and/or freeze-thawing and the like, after which a crude extract of the protein is obtained by centrifugation or filtration. The buffer solution may contain a protein denaturant such as urea or guanidine hydrochloride and a surfactant such as Triton X-100™. When the protein is secreted in the culture broth, the bacterium or cells are separated from the supernatant by a method known per se, and the supernatant is collected, after completion of cultivation.

Purification of the protein contained in the thus-obtained culture supernatant or extract can be performed by an appropriate combination of methods of separation/purification known per se. These commonly known methods of separation/purification include methods based on solubility, such as salting-out and solvent precipitation; methods based mainly on differences in molecular weight, such as dialysis, ultrafiltration, gel filtration, and SDS-polyacrylamide gel electrophoresis; methods based on differences in electric charge, such as ion exchange chromatography; methods based on specific affinity, such as affinity chromatography; methods based on differences in hydrophobicity, such as reverse phase high performance liquid chromatography; methods based on differences in isoelectric point, such as isoelectric focusing; and the like.

When the protein thus obtained is a free form, the free form can be converted to a salt by a method known per se or a method based thereon; conversely, when the protein is obtained in the form of a salt, the salt can be converted to a free form or another salt by a method known per se or a method based thereon.

The protein produced by the transformant can be treated with a suitable protein-modifying enzyme before or after the purification, so as to make an optionally chosen modification or to partially remove a polypeptide. As the protein-modifying enzyme used, for example, trypsin, chymotrypsin, arginyl endopeptidase, protein kinase, glycosidase and the like are used.

The presence of the protein of the present invention thus obtained can be confirmed by an enzyme immunoassay, Western blotting and the like using a specific antibody.

The antibody against a protein or partial peptide used in the present invention or a salt thereof may be a polyclonal antibody or a monoclonal antibody, as long as it is an antibody capable of recognizing the protein or partial peptide used in the present invention or a salt thereof.

The antibody against a protein or partial peptide used in the present invention or a salt thereof (in the explanation of the antibody, these are sometimes simply abbreviated as the protein of the present invention) can be produced using the protein of the present invention as the antigen according to an antibody or antiserum production method known per se. A commercially available supply may be used.

The protein comprising the same or substantially the same amino acid sequence as the amino acid sequence shown by SEQ ID NO:23 (hereinafter also referred to as FBL2), used in the present invention, may be a protein derived from any cells [for example, liver cells, splenocytes, nerve cells, glial cells, β cells of pancreas, bone marrow cells, mesangial cells, Langerhans' cells, epidermic cells, epithelial cells, goblet cells, endothelial cells, smooth muscle cells, fibroblasts, fibrocytes, myocytes, adipocytes, immune cells (e.g., macrophages, T cells, B cells, natural killer cells, mast cells, neutrophils, basophils, eosinophils, monocytes), megakaryocytes, synovial cells, chondrocytes, bone cells, osteoblasts, osteoclasts, mammary gland cells, hepatocytes or interstitial cells or the corresponding precursor cells, stem cells, cancer cells and the like] of humans or other warm-blooded animals (for example, guinea pigs, rats, mice, chickens, rabbits, pigs, sheep, cattle, monkeys and the like), or from any tissues where such cells are present, for example, the brain or each region of the brain (e.g., olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, muscle, lung, gastrointestinal tract (e.g., large intestine, small intestine), blood vessel, heart, thymus, spleen, submandibular gland, peripheral blood, prostate, testis, ovary, placenta, uterus, bone, joint, skeletal muscle and the like], and may also be a synthetic protein.

As substantially the same amino acid sequence as the amino acid sequence shown by SEQ ID NO:23, an amino acid sequence showing a homology of about 50% or more, preferably about 60% or more, more preferably about 70% or more, still more preferably about 80% or more, particularly preferably about 90% or more, and most preferably about 95% or more, to the amino acid sequence shown by SEQ ID NO:23 and the like can be mentioned.

As the protein comprising substantially the same amino acid sequence as the amino acid sequence shown by SEQ ID NO:23, for example, a protein having substantially the same amino acid sequence as the amino acid sequence shown by SEQ ID NO:23, and having substantially the same quality of property as a protein comprising the amino acid sequence shown by SEQ ID NO:23 and the like are preferable. As examples of substantially the same amino acid sequence as the amino acid sequence shown by SEQ ID NO:23, the amino acid sequence shown by SEQ ID NO:34 and the like can be mentioned.

The homology of an amino acid sequence can be calculated using the homology calculation algorithm NCBI BLAST (National Center for Biotechnology Information Basic Local Alignment Search Tool).

Production of FBL2 may be performed in the same manner as the production method for the protein of the present invention or a partial peptide thereof or a salt thereof.

The polynucleotide that encodes FBL2 may be any one comprising a base sequence that encodes FBL2. The polynucleotide is preferably a DNA. The DNA may be any of a genomic DNA, a genomic DNA library, a cDNA derived from the above-described cell or tissue, a cDNA library derived from the above-described cell or tissue, and a synthetic DNA.

The vector used for the library may be any of bacteriophage, plasmid, cosmid, phagemid and the like. The vector can also be directly amplified using a total RNA or mRNA fraction prepared from the aforementioned cells/tissue by Reverse Transcriptase Polymerase Chain Reaction (hereinafter abbreviated as the RT-PCR method).

The DNA that encodes FBL2 may be any one, for example, a DNA comprising the base sequence shown by SEQ ID NO:24 or SEQ ID NO:35, or a DNA that encodes a protein comprising a base sequence that hybridizes to the base sequence shown by SEQ ID NO:24 or SEQ ID NO:35 under high stringent conditions, and having substantially the same quality of property as the above-described protein comprising the amino acid sequence shown by SEQ ID NO:23 or SEQ ID NO:34.

As the DNA capable of hybridizing to the base sequence shown by SEQ ID NO:24 or SEQ ID NO:35 under high stringent conditions, for example, a DNA comprising a base sequence showing a homology of about 50% or more, preferably about 60% or more, more preferably about 70% or more, still more preferably about 80% or more, particularly preferably about 90% or more, and most preferably about 95% or more, to the base sequence shown by SEQ ID NO:24 or SEQ ID NO:35, and the like are used.

The homology of a base sequence can be calculated using the homology calculation algorithm NCBI BLAST (National Center for Biotechnology Information Basic Local Alignment Search Tool) under the following conditions (expectancy=10; gap allowed; filtering=ON; match score=1; mismatch score=−3).

Hybridization can be performed according to a method known per se or a method based thereon, for example, a method described in Molecular Cloning, 2nd (J. Sambrook et al., Cold Spring Harbor Lab. Press, 1989) and the like. When a commercially available library is used, hybridization can be performed according to the method described in the instruction manual attached thereto. More preferably, hybridization can be performed under high stringent conditions.

High-stringent conditions refer to, for example, conditions involving a sodium concentration of about 19 to 40 mM, preferably about 19 to 20 mM, and a temperature of about 50 to 70° C., preferably about 60 to 65° C. In particular, a case wherein the sodium concentration is about 19 mM and the temperature is about 65° C. is most preferable.

More specifically, as the DNA that encodes a protein comprising the amino acid sequence shown by SEQ ID NO:23, a DNA comprising the base sequence shown by SEQ ID NO:24 and the like are used; as the DNA that encodes a protein comprising the amino acid sequence shown by SEQ ID NO:34, a DNA comprising the base sequence shown by SEQ ID NO:35 and the like are used.

Cloning of the DNA that encodes FBL2 may be performed in the same manner as the above-described cloning of the protein of the present invention.

The protein of the present invention (including the protein of the present invention, a partial peptide thereof and a salt thereof) is considered to serve as a substrate for the SCF complex (S-phase kinase-associated protein 1A (Skp1)-Cullin1-Ring box 1 (Rbx1) complex), a kind of Cullin-based E3 complex in the ubiquitin system, and to be ubiquitinated by binding to FBL2, a kind of F-box protein, which is a constituent of this SCF complex. Therefore, (a) a compound that promotes the ubiquitination of the protein of the present invention or a salt thereof, (b) a compound that promotes the degradation of the protein of the present invention by proteasome, or a salt thereof, (c) a compound that promotes the binding of FBL2 and the protein of the present invention, or a salt thereof, (d) a compound that promotes the binding of the SCF complex (preferably a complex comprising FBL2) and the protein of the present invention, or a salt thereof, or (e) a compound that promotes the expression of FBL2 or the expression of the gene for the protein, or a salt thereof, can be used as, for example, a safe prophylactic/therapeutic agent for neurodegenerative diseases [e.g., Alzheimer's disease (familial Alzheimer's disease, juvenile Alzheimer's disease, solitary Alzheimer's disease and the like) and the like] and the like. Also, the protein of the present invention, FBL2 and the gene therefor are useful as, for example, screening reagents for a prophylactic/therapeutic agent for neurodegenerative disease.

In particular, (a) a compound that promotes the ubiquitination of the protein of the present invention (including the protein of the present invention, a partial peptide thereof and a salt thereof) or a salt thereof can be used as, for example, a safe prophylactic/therapeutic agent for neurodegenerative diseases [e.g., Alzheimer's disease (familial Alzheimer's disease, juvenile Alzheimer's disease, solitary Alzheimer's disease and the like) and the like], diabetes mellitus (e.g., type II diabetes mellitus) and the like. The protein of the present invention is also useful as, for example, a screening reagent for a prophylactic/therapeutic agent for diabetes mellitus (e.g., type II diabetes mellitus).

(1) Screening for Drug Candidate Compound for Disease
(1a) Screening Method for a Compound that Promotes the Ubiquitination of the Protein of the Present Invention or a Salt Thereof, Comprising Using the Protein For example, by comparing (i) the ubiquitination activity of the protein of the present invention and (ii) the ubiquitination activity of a mixture of the protein of the present invention and a test compound, a compound that promotes the ubiquitination of the protein of the present invention or a salt thereof is screened for.

Specifically, for example, (i') when cells capable of producing the protein of the present invention are cultured, and (ii') when cells capable of producing the protein of the present invention are cultured in the presence of a test compound, the cells are disrupted after cultivation, the protein of the present invention is recovered from the disruption liquid, the amount of ubiquitin bound to the protein of the present invention recovered is measured according to a commonly known method (e.g., use of an ELISA specific for ubiquitin) and compared. A test compound that increases the amount of ubiquitin bound is selected as a compound that promotes, the ubiquitination.

For example, a test compound that promotes the ubiquitination activity in the case (ii) above by about 20% or more, preferably 30% or more, more preferably about 50% or more, compared to the case (i) above can be selected as a compound that promotes the ubiquitination of the protein of the present invention.

(1b) Screening Method for a Compound that Promotes the Degradation of the Protein of the Present Invention by Proteasome or a Salt Thereof, Comprising Using the Protein For example, by comparing (i) the amount of the protein of the present invention remaining undegraded and (ii) the amount of the protein of the present invention remaining undegraded in a mixture of the protein of the present invention and a test compound, a compound that promotes the degradation of the protein of the present invention or a salt thereof is screened for.

Specifically, for example, (i') when cells capable of producing the protein of the present invention are cultured, and (ii') when cells capable of producing the protein of the present invention are cultured in the presence of a test compound, the cells are disrupted after cultivation, the protein of the present invention is recovered from the disruption liquid, and the residual amount of the protein of the present invention recovered is measured according to a commonly known method (e.g., use of an ELISA system capable of specifically quantifying the protein of the present invention) and compared. Here, if the residual amount of the protein of the present invention decreases in (ii') above than in (i') above, whether or not this reduction is inhibited by a proteasome inhibitor (e.g., MG132) is determined according to a commonly known method. If the reduction is inhibited by the proteasome inhibitor (e.g., MG132), the test compound can be selected as a compound that promotes the degradation of the protein by proteasome.

For example, a test compound that promotes the degradation activity in the case (ii) above by about 20% or more, preferably 30% or more, more preferably about 50% or more, compared to the case (i) above can be selected as a compound that promotes the degradation of the protein of the present invention by proteasome.

(1c) Screening Method for a Compound that Promotes the Binding of FBL2 and the Protein of the Present Invention or a Salt Thereof, Comprising Using FBL2 and the Protein For example, by comparing (i) the amount of the protein of the present invention co-precipitated with FBL2 and (ii) the amount of the protein of the present invention co-precipitated with FBL2 in a mixture of the protein of the present invention and a test compound, a compound that promotes the binding of FBL2 and the protein of the present invention or a salt thereof is screened for.

Specifically, for example, (i') when cells capable of producing the protein of the present invention are cultured, and (ii') when cells capable of producing the protein of the present invention are cultured in the presence of a test compound, FBL2 is precipitated according to a commonly known method (e.g., use of an antibody specific for FBL2 and the like), and the amount of the protein of the present invention co-precipitated with the precipitate is measured according to a commonly known method (e.g., use of an ELISA system capable of specifically quantifying the protein of the present invention) and compared.

For example, a test compound that promotes the amount co-precipitated in the case (ii) above by about 20% or more, preferably 30% or more, more preferably about 50% or more, compared to the case (i) above can be selected as a compound that promotes the binding of FBL2 and the protein of the present invention.

(1d) Screening Method for a Compound that Promotes the Binding of the SCF Complex (Preferably a Complex Comprising FBL2) and the Protein of the Present Invention or a Salt Thereof, Comprising Using the SCF Complex and the Protein For example, by comparing (i) the amount of the protein of the present invention co-precipitated with the SCF complex (preferably a complex comprising FBL2) and (ii) the amount of the protein of the present invention co-precipitated with the SCF complex (preferably a complex comprising FBL2) in a mixture of the protein of the present invention and a test compound, a compound that promotes the binding of the SCF complex and the protein of the present invention or a salt thereof is screened for.

Specifically, for example, (i') when cells capable of producing the protein of the present invention are cultured, and (ii') when cells capable of producing the protein of the present invention are cultured in the presence of a test compound, the SCF complex is precipitated according to a commonly known method (e.g., use of an antibody specific for the SCF complex and the like), and the amounts of the protein of the present invention co-precipitated with the precipitate are measured according to a commonly known method (e.g., use of an ELISA system capable of specifically quantifying the protein of the present invention) and compared.

For example, a test compound that promotes the amount co-precipitated in the case (ii) above by about 20% or more, preferably 30% or more, more preferably about 50% or more, compared to the case (i) above can be selected as a compound that promotes the binding of the SCF complex and the protein of the present invention.

(1e) Screening Method for a Compound that Promotes the Expression of the Protein or a Salt Thereof, Comprising Using FBL2, and Screening Method for a Compound that Promotes the Expression of the Gene for the Protein or a Salt Thereof, Comprising Using a Polynucleotide that Encodes the FBL2 Gene.

For example, a screening method comprising comparing (i) a case where cells capable of producing FBL2 are cultured and (ii) a case where cells capable of producing FBL2 are cultured in the presence of a test compound can be mentioned.

In the above-described method, the expression level of the above-described gene (specifically, protein content of FBL2 or the amount of mRNA that encodes the above-described protein) is measured and compared in cases (i) and (ii).

Protein contents can be measured by a commonly known method, for example, by measuring the above-described protein in cell extract and the like according to a method such as Western blot analysis or ELISA or a method based thereon using an antibody that recognizes FBL2.

The amount of mRNA can be measured according to a commonly known method, for example, Northern hybridization using as the probe a nucleic acid comprising SEQ ID NO:24 or SEQ ID NO:35 or a portion thereof, or a PCR method using as the primer a nucleic acid comprising SEQ ID NO:24 or SEQ ID NO:35 or a portion thereof or a method based thereon.

For example, a test compound that increases the expression level in the case (ii) above by about 20% or more, preferably 30% or more, more preferably about 50% or more, compared to the case (i) above can be selected as a compound that promotes the expression of FBL2 or the expression of the gene for the protein.

In the screenings (1a) to (1e) above, the protein of the present invention used is produced by culturing cells capable of producing the protein of the present invention and the like. Furthermore, a culture broth of the above-described cells, a supernatant thereof, a cell disruption product and the like may be used.

As the cells capable of producing the protein of the present invention or FBL2, for example, a host transformed with a vector comprising the above-described DNA that encodes the protein of the present invention or FBL2 (transformant) is used. As the host, for example, animal cells such as COS7 cells, CHO cells, and HEK293 cells are preferably used. For the screening, for example, a transformant that allows the protein of the present invention or FBL2 to be secreted extracellularly or to be expressed intracellularly by being cultured by the method described above is preferably used. The method of culturing the cells capable of expressing the protein of the present invention or FBL2 is the same as the above-described method of culturing the transformant of the present invention.

In the screenings (1a) to (1e) above, the SCF complex used is the same as that described above.

As examples of the test compound, peptides, proteins, antibodies, non-peptide compounds, synthetic compounds, fermentation products, cell extract, plant extract, animal tissue extract, plasma and the like can be mentioned. The test compound may have formed a salt; as the salt of the test compound, physiologically acceptable metal salts, ammonium salts, salts with organic bases, salts with inorganic acids, salts with organic acids, salts with basic or acidic amino acids and the like can be mentioned. As preferable examples of the salt with a metal, alkali metal salts, for example, sodium salt and potassium salt; alkaline earth metal salts such as calcium salt, magnesium salt, and barium salt; aluminum salt, and the like can be mentioned. As preferable examples of the salt with an organic base, salts with, for example, trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like, can be mentioned. As preferable examples of the salt with an inorganic acid, salts with, for example, hydrochloric acid, hydrobromic acid, nitric acid, sulfuric acid, phosphoric acid and the like, can be mentioned. As preferable examples of the salt with an organic acid, salts with, for example, formic acid, acetic acid, trifluoroacetic acid, propionic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like, can be mentioned. As preferable examples of the salt with a basic amino acid, salts with, for example, arginine, lysine, ornithine and the like, can be mentioned; as preferable examples of the salt with an acidic amino acid, salts with, for example, aspartic acid, glutamic acid and the like, can be mentioned.

The screening kit of the present invention comprises the protein of the present invention or cells capable of producing the protein of the present invention, or (and) FBL2 or cells capable of producing FBL2.

A compound obtained using the screening method or screening kit of the present invention or a salt thereof is selected from among the above-described test compounds, for example, peptides, proteins, antibodies, non-peptide compounds, synthetic compounds, fermentation products, cell extract, plant extract, animal tissue extract, plasma and the like, and has prophylactic/therapeutic action on neurodegenerative disease.

As the salt of the compound, the same as the above-described salt of the test compound of the present invention is used.

A compound that promotes the degradation of the protein of the present invention by proteasome or a salt thereof, a compound that promotes the binding of FBL2 and the protein of the present invention or a salt thereof, a compound that promotes the binding of the SCF complex and the protein of the present invention or a salt thereof, or a compound that promotes the expression of FBL2 or the expression of the gene for the protein or a salt thereof, obtained using the screening method or screening kit of the present invention has, for example, a prophylactic/therapeutic action on neurodegenerative diseases [e.g., Alzheimer's disease (familial Alzheimer's disease, juvenile Alzheimer's disease, solitary Alzheimer's disease and the like) and the like] and the like.

A compound that promotes the ubiquitination of the protein of the present invention or a salt thereof, obtained using the screening method or screening kit of the present invention has, for example, a prophylactic/therapeutic action on neurodegenerative diseases [e.g., Alzheimer's disease (familial Alzheimer's disease, juvenile Alzheimer's disease, solitary Alzheimer's disease and the like) and the like], diabetes mellitus (e.g., type II diabetes mellitus) and the like.

When (i) a compound that promotes the ubiquitination of the protein of the present invention or a salt thereof, (ii) a compound that promotes the degradation of the protein of the present invention by proteasome or a salt thereof, (iii) a compound that promotes the binding of FBL2 and the protein of the present invention or a salt thereof, (iv) a compound that promotes the binding of the SCF complex and the protein of the present invention or a salt thereof, or (v) a compound that promotes the expression of FBL2 or the expression of the protein gene or a salt thereof is used as the above-described prophylactic/therapeutic agent, it can be prepared as a pharmaceutical preparation according to a conventional method.

For example, as the composition for oral administration, solid or liquid dosage forms, specifically tablets (including sugar-coated tables and film-coated tablets), pills, granules, powders, capsules (including soft capsules), syrups, emulsions, suspensions and the like can be mentioned. Such a composition is produced by a method known per se, and contains a carrier, a diluent or a filler normally used in the field of pharmaceutical making. For example, as the carrier or filler for tablets, lactose, starch, sucrose, magnesium stearate and the like can be used.

As examples of the composition for parenteral administration, injections, suppositories and the like are used; the injections include dosage forms such as intravenous injections, subcutaneous injections, intracutaneous injections, intramuscular injections, drip infusion injections and intraarticular injections. Such an injection is prepared according to a method known per se by, for example, dissolving, suspending or emulsifying the above-described compound or a salt thereof in a sterile aqueous or oily solution normally used for injections. As examples of the aqueous solution for injection, physiological saline, an isotonic solution containing glucose or another auxiliary drug, and the like can be used, which may be used in combination with an appropriate solubilizer, for example, an alcohol (e.g., ethanol), a polyalcohol (e.g., propylene glycol, polyethylene glycol), a non-ionic surfactant [e.g., polysorbate 80, HCO-50 (polyoxyethylene (50 mol) adduct of hydrogenated castor oil)] and the like. As examples of the oily solution, sesame oil, soybean oil and the like can be used, which may be used in combination with a solubilizer such as benzyl benzoate or benzyl alcohol. The injectable preparation prepared is normally filled in an appropriate ampoule. A suppository used for rectal administration is prepared by mixing the above-described antibody or a salt thereof in an ordinary suppository base.

The above-described pharmaceutical composition for oral administration or for parenteral administration is conveniently prepared in a medication unit dosage form suitable for the dosage of the active ingredient. As examples of such a medication unit dosage form, tablets, pills, capsules, injections (ampoules), suppositories and the like can be mentioned; it is preferable that normally 5 to 500 mg, particularly 5 to 100 mg for injections or 10 to 250 mg for other dosage forms, per medication unit dosage form, of the above-described compound be contained.

Each of the aforementioned compositions may contain another active ingredient, as long as no undesirable interaction is produced when blended with the above-described compound.

Because the preparation thus obtained is safe and of low toxicity, it can be orally or parenterally administered to, for example, humans or warm-blooded animals (for example, mice, rats, rabbits, sheep, pigs, cattle, horses, chicken, cats, dogs, monkeys, chimpanzees and the like).

The dosage of the compound or a salt thereof varies depending on the action thereof, target disease, recipient, symptoms, route of administration and the like; for example, when any of the compounds of (i) to (v) above or a salt thereof is orally administered for the purpose of treating Alzheimer's disease, about 0.1 to 100 mg, preferably about 1.0 to 50 mg, more preferably about 1.0 to 20 mg, per day of the compound or a salt thereof is administered for an adult (weighing 60 kg). In the case of parenteral administration, the dosage of the compound or a salt thereof varies depending on target disease, recipient, symptoms, route of administration and the like; for example, when any of the compounds of (i) to (v) above or a salt thereof is administered in the form of an injection for the purpose of treating Alzheimer's disease, about 0.01 to 30 mg, preferably about 0.1 to 20 mg, more preferably about 0.1 to 10 mg, per day of the compound or a salt thereof is conveniently administered by intravenous injection for an adult (weighing 60 kg). In the case of other animals, a dosage converted per 60 kg of body weight can be administered.

(2) Quantitation of FBL2

Because the antibody against FBL2 (hereinafter sometimes abbreviated as the antibody of the present invention) is capable of specifically recognizing FBL2, it can be used for quantitation of FBL2 in a test liquid, particularly for quantitation by sandwich immunoassay and the like.

The method for quantifying FBL2 using the above-described antibody is not to be limited particularly; any method of measurement can be used, so long as the amount of antibody, antigen or antibody-antigen complex corresponding to the amount of antigen (for example, protein content) in a test liquid can be detected by a chemical or physical means and can be calculated from a standard curve generated using standard solutions containing known amounts of the antigen. For example, nephelometry, the competitive method, immunonometric method, and sandwich method are advantageously used, and the sandwich method described below is particularly preferable in terms of sensitivity and specificity.

As the labeling agent used for the assay methods using a labeled substance, for example, a radioisotope, an enzyme, a fluorescent substance, a luminescent substance and the like are used. As the radioisotope, for example, [$^{125}$I], [$^{131}$I], [$^{3}$H], [$^{14}$C] and the like are used. As the enzyme described above, stable enzymes with a high specific activity are preferred; for example, β-galactosidase, β-glucosidase, alkaline phosphatase, peroxidase, malate dehydrogenase and the like are used. As the fluorescent substance, fluorescamine, fluorescein isothiocyanate and the like are used. As the luminescent substance, for example, luminol, luminol derivatives, luciferin, lucigenin and the like are used. Furthermore, a biotin-avidin system may also be used for the binding of an antibody or antigen and the labeling agent.

For insolubilization of the antigen or antibody, physical adsorption may be used, and chemical binding methods conventionally used to insolubilize or immobilize proteins, enzymes and the like may be used as well. As the carrier, insoluble polysaccharides such as agarose, dextran, and cellulose; synthetic resins such as polystyrene, polyacrylamide, and silicone, or glass and the like can be mentioned.

In the sandwich method, an insolubilized monoclonal antibody of FBL2 is reacted with a test liquid (primary reaction), then reacted with a labeled monoclonal antibody of FBL2 (secondary reaction), after which the activity of the labeling agent on the insolubilizing carrier is measured, whereby the protein content of FBL2 in the test liquid can be quantified. The order of the primary and secondary reactions may be reversed, and the reactions may be performed simultaneously or at a time lag. The labeling agent and the method for insolubilization can be the same as those described above. In the immunoassay by the sandwich method, the antibody used for the antibody for solid phase or the antibody for labeling is not necessarily from one kind, but a mixture of two or more kinds of antibodies may be used to increase the measurement sensitivity.

In the assay of the protein of FBL2 by the sandwich method, the monoclonal antibodies of FBL2 used for the primary and secondary reactions are preferably antibodies having mutually different sites for FBL2 binding. That is, for the antibodies used in the primary and secondary reactions, for example, when the antibody used in the secondary reaction recognizes the C terminus of FBL2, the antibody used in the primary reaction is preferably an antibody that recognizes a portion other than the C terminus, for example, the N terminus.

The monoclonal antibody of the present invention can be used for assay systems other than the sandwich method, for example, the competitive method, immunometric method, nephelometry and the like. The competitive method, immunometric method, nephelometry and the like can be performed according to a commonly known method.

Furthermore, if an increase or decrease in the concentration of FBL2 is detected by quantifying the concentration of FBL2 using the above-described antibody against FBL2, the subject animal can be diagnosed as having or being likely to contract, for example, a neurodegenerative disease [e.g., Alzheimer's disease (familial Alzheimer's disease, juvenile Alzheimer's disease, solitary Alzheimer's disease and the like) and the like] and the like.

(3) Gene Diagnostic Reagents

Because a DNA that encodes FBL2 is capable of detecting an abnormality (gene abnormality) in a DNA or mRNA that encodes the protein of FBL2 or a partial peptide thereof in humans or warm-blooded animals (for example, rats, mice, guinea pigs, rabbits, chicken, sheep, pigs, cattle, horses, cats, dogs, monkeys, chimpanzees and the like) when used as, for example, a probe, it is useful as a gene diagnostic reagent for, for example, damage, mutation or decreased expression in the DNA or mRNA, an increase or overexpression in the DNA or mRNA and the like.

The above-described gene diagnosis can be performed by, for example, Northern hybridization known per se and the PCR-SSCP method (Genomics, Vol. 5, pp. 874-879 (1989), Proceedings of the National Academy of Sciences of the USA, Vol. 86, pp. 2766-2770 (1989)) and the like.

For example, if an overexpression or decreased expression is detected by Northern hybridization, or if a DNA mutation is detected by the PCR-SSCP method, the subject animal can be diagnosed as having, for example, a neurodegenerative disease [e.g., Alzheimer's disease (familial Alzheimer's disease, juvenile Alzheimer's disease, solitary Alzheimer's disease and the like) and the like] and the like.

In the description, the codes of bases and amino acids are denoted in accordance with the IUPAC-IUB Commission on Biochemical Nomenclature or by the common codes in the art, examples of which are shown below. For amino acids that may have an optical isomer, the L-form is presented unless otherwise indicated.

| | |
|---|---|
| DNA | deoxyribonucleic acid |
| cDNA | complementary deoxyribonucleic acid |
| A | adenine |
| T | thymine |
| G | guanine |
| C | cytosine |
| RNA | ribonucleic acid |
| mRNA | messenger ribonucleic acid |
| dATP | deoxyadenosine triphosphate |
| dTTP | deoxythymidine triphosphate |
| dGTP | deoxyguanosine triphosphate |
| dCTP | deoxycytidine triphosphate |
| ATP | adenosine triphosphate |
| EDTA | ethylenediaminetetraacetic acid |
| SDS | sodium dodecyl sulfate |
| Gly | glycine |
| Ala | alanine |
| Val | valine |
| Leu | leucine |
| Ile | isoleucine |
| Ser | serine |
| Thr | threonine |
| Cys | cysteine |
| Met | methionine |
| Glu | glutamic acid |
| Asp | aspartic acid |
| Lys | lysine |
| Arg | arginine |
| His | histidine |
| Phe | phenylalanine |
| Tyr | tyrosine |
| Trp | tryptophan |
| Pro | proline |
| Asn | asparagine |
| Gln | glutamine |
| pGlu | pyroglutamic acid |
| Sec | selenocysteine |

The sequence identification numbers in the sequence listing of the present description show the following sequences.
[SEQ ID NO:1]
Shows the amino acid sequence of CTFα protein.
[SEQ ID NO:2]
Shows the amino acid sequence of CTFβ protein.
[SEQ ID NO:3]
Shows the amino acid sequence of APP protein.
[SEQ ID NO:4]
Shows the base sequence of a primer used in Example 1 and Example 3.

[SEQ ID NO:5]
Shows the base sequence of a primer used in Example 1.
[SEQ ID NO:6]
Shows the base sequence of a primer used in Example 1.
[SEQ ID NO:7]
Shows the base sequence of an siRNA used in Example 2.
[SEQ ID NO:8]
Shows the base sequence of an siRNA used in Example 2.
[SEQ ID NO:9]
Shows the base sequence of a primer used in Example 3.
[SEQ ID NO:10]
Shows the base sequence of a primer used in Example 4.
[SEQ ID NO:11]
Shows the base sequence of a primer used in Example 4.
[SEQ ID NO:12]
Shows the base sequence of a primer used in Example 4.
[SEQ ID NO:13]
Shows the base sequence of a primer used in Example 4.
[SEQ ID NO:14]
Shows the base sequence of a primer used in Example 4.
[SEQ ID NO:15]
Shows the base sequence of a primer used in Example 4.
[SEQ ID NO:16]
Shows the base sequence of a primer used in Example 4.
[SEQ ID NO:17]
Shows the base sequence of a primer used in Example 4.
[SEQ ID NO:18]
Shows the base sequence of a primer used in Example 4.
[SEQ ID NO:19]
Shows the base sequence of a primer used in Example 1.
[SEQ ID NO:20]
Shows the base sequence that encodes CTFα protein.
[SEQ ID NO:21]
Shows the base sequence that encodes CTFβ protein.
[SEQ ID NO:22]
Shows the base sequence that encodes APP protein.
[SEQ ID NO:23]
Shows the amino acid sequence of human FBL2 (hFBL2).
[SEQ ID NO:24]
Shows the base sequence that encodes human FBL2 (hFBL2).
[SEQ ID NO:25]
Shows the base sequence of a primer used in Example 5.
[SEQ ID NO:26]
Shows the base sequence of a primer used in Example 5.
[SEQ ID NO:27]
Shows the base sequence of a primer used in Example 5.
[SEQ ID NO:28]
Shows the base sequence of a primer used in Example 5.
[SEQ ID NO:29]
Shows the base sequence of a primer used in Example 5.
[SEQ ID NO:30]
Shows the base sequence of a primer used in Example 5.
[SEQ ID NO:31]
Shows the base sequence of a primer used in Example 5.
[SEQ ID NO:32]
Shows the base sequence of a primer used in Example 5.
[SEQ ID NO:33]
Shows the base sequence of a primer used in Example 5.
[SEQ ID NO:34]
Shows the amino acid sequence of mouse FBL2 (mFBL2).
[SEQ ID NO:35]
Shows the base sequence that encodes mouse FBL2 (mFBL2).

EXAMPLES

The present invention is hereinafter described in more detail by means of the following Examples, which, however, are not to be construed as limiting the scope of the invention.

Example 1

Effects of FBL2 on Aβ Production

To amplify the human type FBL2 (hFBL2) gene, PCR was performed using synthetic primers (SEQ ID NO:19 and SEQ ID NO:4), pyrobest (Takara) as the enzyme, and a quick clone human whole brain cDNA (CLONTECH) as the template under the following conditions (1) to (3) to yield a specific PCR product.
(1) 94° C. 5 minutes
(2) 94° C. 30 seconds—56° C. 30 seconds—72° C. 2 minutes in 35 cycles
(3) 72° C. 7 minutes The PCR product obtained was cloned into pcDNA3.1/V5-His TOPO (Invitrogen) and transformed to *Escherichia coli* DH5α. PCR was performed using the colony obtained, synthetic primers (SEQ ID NO:5 and SEQ ID NO:6) and ExTaq (Takara) as the enzyme to yield a PCR product. After the substrate in this PCR product was degraded with ExoSAP-IT (Amersham Pharmacia), a sequencing reaction was performed using this as the template and BigDye Terminator v3.1 Cycle Sequencing Ready Reaction (ABI), and the sequencing product was analyzed using the 3100 Genetic analyzer (ABI). Colonies of the right sequence were cultured with LB medium, and the vector was recovered using the QIAGEN endofree maxi kit (QIAGEN).

3 µg of this hFBL2 gene expression vector (hereinafter referred to as the hFBL2 expression vector) and 2 µg of the pcDNA3.1 vector harboring the amyloid precursor protein (hereinafter referred to as APP695) gene, which consists of 695 amino acids (hereinafter referred to as the hAPP695 expression vector), was transduced to human neuroblastoma SK-N-AS cells (purchased from ATCC) using Nucleofector (AMAXA). For control, the GFP expression vector (pQBI-25-fA: Wako Pure Chemical Industries) was used in place of the hFBL2 expression vector and transduced to SK-N-AS cells in the same manner as described above.

Each type of transduced cells were sown to a type I collagen coated 24-well plate (IWAKI) at 300000 cells/well, and cultured overnight, after which the medium was exchanged with a fresh supply, and the cells were further cultured overnight. Using 100 µl of the culture supernatant as the test sample, Aβ contents were measured by the method described below.

By immunizing a BALB/C mouse with β-amyloid (11-28) in accordance with the method described in Example 7 of Official Gazette for WO 94/17197, the mouse monoclonal antibody BNT-77a (Biochemistry, Vol. 34, pp. 10272-10278, 1995) was obtained.

A 0.1 M carbonic acid buffer solution (pH 9.6 solution) containing 15 µg/ml BNT-77a was dispensed to a 96-well microplate at 100 µl per well, and the plate was allowed to stand at 4° C. for 24 hours. The excess binding portions of the wells were inactivated by adding 300 µl of Block Ace (Dainippon Pharmaceutical), previously diluted 4 fold with PBS, and allowing them to stand at 4° C. for 24 hours, to yield a BNT-77a (primary antibody) immobilized plate.

In measuring Aβx-40 contents, a series of dilutions of Aβ 1-40 (Peptide Institute), diluted with buffer EC [a 0.02 M phosphate buffer solution containing 10% Block Ace, 0.2%

BSA, 0.4 M NaCl, 0.05% CHAPS, 2 mM EDTA, and 0.05% NaN3, pH 7], and 100 μl of a test sample were added to the BNT-77a immobilized plate, and they were reacted at 4° C. for 24 hours. After the plate was washed with PBS, 100 μl of BA-27a-HRP (described in Example 8 of Official Gazette for WO 94/17197), previously diluted 1000 fold with buffer C [a 0.02 M phosphate buffer solution containing 1% BSA, 0.4 M NaCl, and 2 mM EDTA, pH 7], as the secondary antibody, was added, and they were reacted at room temperature for 6 hours. After the plate was washed with PBS, 100 μl of the TMB microwell peroxidase substrate system (KIRKEG-AARD & PERRY LAB, INC) was added, and they were reacted at room temperature for 10 minutes. After the reaction was stopped by the addition of 100 μl of 1 M phosphoric acid, enzyme activity on the solid phase was determined by measuring the absorbance at 450 nm using a plate reader (SPECTRAMAX190, Molecular Device).

Aβ x-42 contents were measured by adding a series of dilutions of Aβ 1-42 (Peptide Institute), diluted with buffer EC, and 100 μl of a test sample to the BNT-77a-immobilized plate, using BC-05a-HRP (described in Example 8 of Official Gazette for WO 94/17197) as the secondary antibody, in the same manner as the above-described measurement of Aβ x-40 contents.

The results are shown below.

The Aβ 40 and Aβ 42 contents in the culture supernatant of controls (cells transfected with the GFP and APP695 expression vector) were 92.4±8.9 pM, and 7.7±1.0 pM, respectively. By contrast, the Aβ 40 and Aβ 42 contents in the culture supernatant of cells transfected with the hFBL2 and APP expression vector were 72.1±1.8 pM, and 6.6±1.0 pM, respectively.

From this, it is seen that Aβ 40 contents and Aβ 42 contents decrease with the expression of the hFBL2 gene.

Example 2

Effects of Suppression of hFBL2 Gene Expression by siRNA on Aβ Production

An siRNA (SEQ ID NO:7) capable of suppressing the expression of hFBL2 gene was transduced into human neuroblastoma IMR-32 cells (purchased from ATCC) using Nucleofector (AMAXA). As a control, an siRNA (SEQ ID NO:8) capable of suppressing the expression of GFP gene was transduced into IMR-32 cells.

Each transduced cells were seeded at 660,000 cells/well on Type I collagen-coated 24-well plates (IWAKI). After overnight culture, the medium was exchanged and the cells were cultured for another 24 to 72 hours. Then, 100 μl of the culture supernatant was used to determine Aβ contents in the supernatant according to the method of Example 1.

The results are shown below.

In GFP-siRNA used as a control, the Aβ40 contents after 24, 48 and 72 hours were 46.6±0.6 pM, 67.5±1.0 pM, and 80.9±1.6 pM, respectively, and the Aβ42 contents were 2.95±0.05 pM, 5.61±0.02 pM, and 11.50±0.44 pM, respectively. By contrast thereto, in the cells transfected with hFBL2-siRNA, the Aβ40 contents after 24, 48 and 72 hours were 52.7±1.5 pM, 68.0±0.3 pM, and 98.4±3.0 pM, respectively, and the Aβ42 contents were 4.40±0.02 pM, 7.44±0.18 pM, and 14.12±1.09 pM, respectively.

These results reveal that the suppression of the expression of hFBL2 gene, which is constantly expressed within cells, with siRNA leads to increased Aβ contents.

Example 3

Binding of hFBL2 Protein and APP Protein

To prepare an hFBL2 expression vector harboring a Flag tag introduced at the N terminus thereof, PCR was performed using synthetic primers (SEQ ID NO:4 and SEQ ID NO:9), pyrobest (Takara) as the enzyme, and the hFBL2 expression vector prepared in Example 1 as the template under the following conditions (1) to (3) to yield a specific PCR product.
(1) 94° C. 5 minutes
(2) 94° C. 30 seconds—55° C. 30 seconds—72° C. 2 minutes in 25 cycles
(3) 72° C. 7 minutes The PCR product obtained was cloned into pcDNA3.1/V5-His TOPO (Invitrogen), and the expression plasmid was isolated using the same method as Example 1.

HEK293A cells were sown to type I collagen coated 6 cm Petri dishes (IWAKI) at 800000 cells/dish, and cultured at 37° C. for 18 hours. To 0.5 ml of OPTI-MEM medium (GIBCO), 22 μl of lipofectamine 2000 (Invitrogen) was added, and the mixture was allowed to stand at room temperature for 5 minutes, after which the mixture was mixed with 0.5 ml of an OPTI-MEM medium supplemented with 5 μg of each of the hAPP695 expression vector (Example 1) and the hFBL2 expression vector harboring a Flag tag, obtained above, and they were reacted at room temperature for 20 minutes. For control, the pCMV2B-control vector (Stratagene) was used. After the reaction, the mixture was added to the cell-sown Petri dishes, the cells were cultured at 37° C. for 4 hours, and the medium was exchanged with a fresh supply, after which the cells were further cultured for 18 hours. To inhibit the degradation via the ubiquitine-proteasome pathway, the proteasome inhibitor MG132 (CALBIOCHEM) was added to obtain a final concentration of 15 μM, and the cells were cultured at 37° C. for 3 hours. The medium was removed, and the cells were washed with 5 ml of PBS two times, after which 1 ml of cell disruption buffer (lysis buffer) (50 mM Tris-HCl (pH 7.5), 150 mM NaCl, 0.5% NP-40, 1 mM β-mercaptoethanol, protease inhibitor cocktail (Roche), 10 μm MG132) was added, and the cells were disrupted. 20 μl of anti-Flag agarose (Sigma), previously equilibrated with the lysis buffer, was added to the supernatant recovered by centrifugation, and they were reacted at 4° C. for 22 hours while rotating. After the cells were washed with 1 ml of the lysis buffer four times, 100 μl of sample buffer (Daiichi Kagaku) was added, and they were treated at 95° C. for 5 minutes. After SDS-polyacrylamide gel electrophoresis, the treated sample was transferred onto PVDF membrane (Millipore), blocking was performed at room temperature for 1.5 hours (50 mM Tris-HCl (pH 7.5), 150 mM NaCl, 5% skimmed milk, 0.1% Tween), after which a primary antibody [anti-APP antibody (22C11: Chemi-Con, 1/1000 diluted), an anti-APP antibody (CT695: Zymed Laboratories, 1/1000 diluted), and an anti-Flag antibody (Sigma, 1/1000 diluted)] were added, and they were reacted at 4° C. for 20 hours. After the primary antibody reaction, the cells were washed with TTBS buffer. [50 mM Tris-HCl (pH 7.5), 150 mM NaCl, 0.1% Tween] three times, a secondary antibody [anti-mouse-HRP antibody (Amersham Pharmacia) and an anti-rabbit-HRP antibody (Santa Cruz Biotechnology): 1/2000 diluted] were added, and they were reacted at room temperature for 1.5 hours. After the reaction, the cells were washed with the TTBS buffer three times, and detection was performed using the ECL plus reagent (Amersham Pharmacia).

As a result, only in the immunoprecipitated fraction that allowed the expression of hFBL2 incorporating a Flag tag, a band corresponding to APP was detected. Furthermore, bands corresponding to the C-terminal fragment a (CTFA) and C-terminal fragment α (CTFα) resulting from cleavage of APP by α-secretase and β-secretase were also detected only in the immunoprecipitated fraction that allowed the expression of hFBL2 incorporating a Flag tag.

From this, it was found that the hFBL2 protein bound to the APP protein, CTFα protein and CTFβ protein.

Example 4

Identification of Specific Substrate for hFBL2

To prepare an hFBL2 expression vector to be used in the Yeast Two-Hybrid system, PCR was performed using synthetic primers (SEQ ID NO:10 and SEQ ID NO:11), pyrobest (Takara) as the enzyme, and the hFBL2 expression vector prepared in Example 1 as the template under the following conditions (1) to (3) to yield a specific PCR product.
(1) 94° C. 5 minutes
(2) 94° C. 30 seconds—55° C. 30 seconds—72° C. 2 minutes in 27 cycles
(3) 72° C. 7 minutes The PCR product obtained was purified using a GFX column (Amersham Pharmacia). This purified PCR product and the pGBKT7 vector (CLONTECH) were treated with the restriction endonucleases NdeI and PstI (Takara), after which both were joined using DNA ligation kit ver2 (Takara), and transformed to *Escherichia coli* DH5α. Then, by the same method as Example 1, the expression vector was isolated.

This vector was transformed to the AH109 strain (CLONTECH) using Yeast Transformation System (CLONTECH) according to the experimental manual attached to the kit. After joining was performed using the Pretransformed Matchmaker human brain cDNA library (CLONTECH) according to the experimental manual attached, the cells were cultured on an SD agar medium not comprising histidine, leucine, or tryptophan at 30° C. for 9 days. Grown colonies were further cultured on an SD agar medium not comprising adenine, histidine, leucine, or tryptophan, but comprising X-α-gal (CLONTECH), at 30° C. for 16 days. X-α-gal positive clones stained blue were again subjected to streak culture on the same SD agar medium, and X-α-gal activity was reconfirmed. For the positive clones, the plasmid was isolated using the RPM Yeast Plasmid Isolation Kit (Q-BIOgene), and with this as the template, and using a synthetic primer (SEQ ID NO:12) and BigDye Terminator v3.1 Cycle Sequencing Ready Reaction (ABI), a sequencing reaction was performed, and the sequencing product was analyzed using the 3100 Genetic analyzer (ABI). As a result of a homology search of the sequences obtained by the sequence analysis, these positive clones were identified as S-phase kinase-associated protein 1A (Skp1) and yippee-like 1 (YPEL1).

To determine whether or not these proteins bind to hFBL2 in cells, the following experiments were performed.

To amplify the human type Skp1 (hSkp1) gene, PCR was performed using synthetic primers (SEQ ID NO:13 and SEQ ID NO:14), pyrobest (Takara) as the enzyme, and quick clone human whole brain cDNA (CLONTECH) as the template under the following conditions (4) to (6) to yield a specific PCR product.
(4) 94° C. 5 minutes
(5) 94° C. 30 seconds—55° C. 30 seconds—72° C. 1 minute in 35 cycles
(6) 72° C. 7 minutes The PCR product obtained was cloned into pcDNA3.1/V5-His TOPO (Invitrogen) and transformed to *Escherichia coli* DH5α. Then, by the same method as Example 1, the expression vector was isolated.

To amplify the human type YPEL1 (hYPEL1) gene, PCR was performed using synthetic primers (SEQ ID NO:15 and SEQ ID NO:16), pyrobest (Takara) as the enzyme, and human brain first-strand cDNA (Human Multiple Tissue cDNA panel 1: CLONTECH) as the template under the following conditions (7) to (9) to yield a specific PCR product.
(7) 94° C. 5 minutes
(8) 94° C. 30 seconds—55° C. 30 seconds—72° C. 2 minutes in 40 cycles
(9) 72° C. 7 minutes The PCR product obtained was cloned into pcDNA3.1/V5-His TOPO (Invitrogen) and transformed to *Escherichia coli* DH5α. Then, by the same method as Example 1, the expression vector was isolated. Furthermore, to prepare an hYPEL1 expression vector having the Myc tag introduced to the N terminus thereof, PCR was performed using synthetic primers (SEQ ID NO:17 and SEQ ID NO:18), pyrobest (Takara) as the enzyme, and the above-described hYPEL1 expression vector as the template under the following conditions (10) to (12) to yield a specific PCR product.
(10) 94° C. 5 minutes
(11) 94° C. 30 seconds—55° C. 30 seconds—72° C. 1 minute in 27 cycles
(12) 72° C. 7 minutes The PCR product obtained was purified using a GFX column (Amersham Pharmacia). This purified PCR product and the pCMV3B vector (Stratagene) were treated with the restriction endonucleases EcoRI and XhoI (Takara), after which both were joined using DNA ligation kit ver2 (Takara), and transformed to *Escherichia coli* DH5α. Then, by the same method as Example 1, the expression vector was isolated.

COS7 cells were sown to 6 cm Petri dishes (Falcon) at 200000 cells/dish, and cultured at 37° C. for 18 hours. 27.5 µl of lipofectamine 2000 (Invitrogen) was added to 0.55 ml of OPTI-MEM medium (GIBCO), and the mixture was allowed to stand at room temperature for 5 minutes, after which 5.5 µg of the hFBL2 expression vector harboring a Flag tag (Example 3) and 5.5 µg of the hSkp1 expression vector, or 5.5 µg of the hFBL2 expression vector harboring a Flag tag (Example 3) and 5.5 µg of the hYPEL1 expression vector harboring the Myc tag, were mixed with 0.55 ml of OPTI-MEM medium, and each mixture was allowed to stand at room temperature for 20 minutes. The mixture was added to the cell-sown Petri dishes, the cells were cultured at 37° C. for 4 hours, and the medium was exchanged with a fresh supply, after which the cells were further cultured for 18 hours. For control, the pCMV2B-control vector (Stratagene) was used in place of the hFBL2 expression vector harboring a Flag tag, and transduced to COS7 cells by the same method as described above.

To inhibit the degradation via the ubiquitine-proteasome pathway, MG132 (CALBIOCHEM) was added to obtain a final concentration of 15 µM, and the cells were cultured at 37° C. for 3 hours. The medium was removed, and the cells were washed with 5 ml of PBS two times, after which 1 ml of cell disruption buffer (lysis buffer) (50 mM Tris-HCl (pH 7.5), 150 mM NaCl, 0.5% NP-40, 1 mM β-mercaptoethanol, protease inhibitor cocktail (Roche), 10 µM MG132) was added, and the cells were disrupted. 20 µl of anti-Flag agarose (Sigma), previously equilibrated with the lysis buffer, was added to the supernatant recovered by centrifugation, and they were reacted at 4° C. for 22 hours while rotating. After the agarose was washed with 1 ml of the lysis buffer four times, 100 μl of sample buffer (Daiichi Kagaku) was added, and they were treated at 95° C. for 5 minutes. After SDS-polyacrylamide gel electrophoresis, the treated sample was transferred onto PVDF membrane, and blocking was performed at room temperature for 1.5 hours (50 mM Tris-HCl (pH 7.5), 150 mM NaCl, 5% skimmed milk, 0.1% Tween), after which a primary antibody [anti-Skp1 antibody (H-163: Santa Cruz Biotechnology, 1/500 diluted) and an anti-Myc antibody (A-14: Santa Cruz Biotechnology, 1/500 diluted)] were added, and they were reacted at 4° C. for 20 hours. After the primary antibody reaction, the membrane was washed with TTBS buffer [50 mM Tris-HCl (pH 7.5), 150 mM NaCl, 0.1% Tween] three times, a secondary antibody [anti-rabbit-HRP antibody (Santa Cruz Biotechnology): 1/2000 diluted] was added, and they were reacted at room temperature for 1.5 hours. After the reaction, the membrane was washed with the TTBS buffer three times, and detection was performed using the ECL plus reagent (Amersham Pharmacia).

As a result, only in the immunoprecipitated fraction that allowed the expression of the hFBL2 incorporating a Flag tag, bands corresponding to hSkp1 and hYPEL1 were detected.

From this, it was found that hFBL2 bound to hSkp1 and hYPEL1.

Example 5

Aβ Production Reduction by FBL2 in Mouse Primary Nerve Cells (1) Preparation of mFBL2 Expression Vector Harboring a Flag Tag To amplify the mouse type FBL2 (mFBL2) gene, PCR was performed using synthetic primers (SEQ ID NO:25 and SEQ ID NO:26), pfuturbo (Takara Shuzo) as the enzyme, and mouse multiple tissue cDNA panel I (BD Bioscience) as the template under the following conditions (1) to (3) to yield a specific PCR product.
(1) 94° C. 5 minutes
(2) 94° C. 30 seconds—56° C. 30 seconds—72° C. 2 minutes in 35 cycles
(3) 72° C. 7 minutes The PCR product obtained was cloned into pcDNA3.2/V5/GW/D-TOPO (Invitrogen) and transformed to *Escherichia coli* DH5α. PCR was performed using the colony obtained, synthetic primers (SEQ ID NO:5 and SEQ ID NO:27) and ExTaq (Takara Shuzo) as the enzyme to yield a PCR product. By the same method as Example 1, the expression vector was isolated from the PCR product obtained (hereinafter referred to as the mFBL2 expression vector). To introduce a Flag tag to the N terminus of the mFBL2 expression vector, PCR was performed using synthetic primers (SEQ ID NO:28 and SEQ ID NO:29), pyrobest (Takara Shuzo) as the enzyme, and the mFBL2 expression vector as the template under the following conditions (4) to (6) to yield a specific PCR product.
(4) 94° C. 5 minutes
(5) 94° C. 30 seconds—55° C. 30 seconds—72° C. 1 minute 30 seconds in 27 cycles
(6) 72° C. 7 minutes The PCR product obtained was purified using a GFX column (Amersham Biosciences). After this purified PCR product and the pCMV2B vector (Stratagene) were treated with the restriction endonucleases EcoRI and XhoI (Takara Shuzo), both were joined using DNA ligation kit ver2 (Takara Shuzo), and transformed to *Escherichia coli* DH5α. By the same method as Example 1, the expression vector was isolated from the PCR product obtained (hereinafter referred to as the mFBL2 expression vector harboring a Flag tag).

(2) Preparation of mFBL2 Expression Lentivirus Vector

An mFBL2 expression lentivirus vector was prepared by the method described below. PCR was performed using synthetic primers (SEQ ID NO:30 and SEQ ID NO:31), Pfuturbo Hotstart DNA Polymerase (Stratagene) as the enzyme, and the mFBL2 expression vector harboring a Flag tag as the template under the following conditions (7) to (9).
(7) 95° C. 2 minutes
(8) 95° C. 30 seconds—58° C. 30 seconds—72° C. 2 minutes in 35 cycles
(9) 72° C. 7 minutes After the amplified DNA was separated by 1.5% agarose gel electrophoresis, a DNA about 1200 bases in length was cut out using a razor, and the DNA was recovered using QIAquick Gel Extraction Kit (QIAGEN). The DNA obtained was cloned to the pCR-BluntII-TOPO vector (Invitrogen) attached to TOPO TA Cloning Kit (Invitrogen) according to the protocol. After this was transduced to *Escherichia coli* TOP10 (Invitrogen) to transform the same, clones having the cDNA insert were selected using a kanamycin-comprising LB agar medium to yield a transformant. Each clone was cultured using a kanamycin-comprising LB medium overnight, and a plasmid DNA was prepared using QIAwell 8 Plasmid Kit (QIAGEN). This was subjected to a sequencing reaction using the BigDye Terminator Cycle Sequencing kit (Applied Biosystem), and the sequencing product was analyzed using the 3100 Genetic analyzer (Applied Biosystem). The vector constructed was named mFBL2-pCR-BluntII-TOPO.

Each of mFBL2-pCR-BluntII-TOPO and the lentivirus expression vector CSII-CMV-MCS (RIKEN BioResource Center) was digested with the restriction endonucleases NotI and XhoI (both from Takara Shuzo), the desired band cleaved was cut out using a razor, and the DNA was recovered using QIAquick Gel Extraction Kit (QIAGEN). The mFBL2 fragment and CSII-CMV-MCS (digested with NotI and XhoI) were joined according to the protocol for DNA Ligation Kit Ver2.1. After this was transduced to *Escherichia coli* TOP10 (Invitrogen) to transform the same, clones having the cDNA insert were selected using an ampicillin-comprising LB agar medium to yield a transformant. Each clone was cultured using an ampicillin-comprising LB medium overnight, and a plasmid DNA was prepared using QIAwell 8 Plasmid Kit (QIAGEN). The plasmid DNA obtained was subjected to a sequencing reaction using the BigDye Terminator Cycle Sequencing kit (Applied Biosystem), and the sequencing product was analyzed using the 3100 Genetic analyzer (Applied Biosystem). The vector obtained was named CSII-CMV-MCS-mFBL2 vector.

(3) Preparation of LacZ Expression Lentivirus Vector

A LacZ expression lentivirus vector was constructed by the method described below.

PCR was performed using synthetic primers (SEQ ID NO:32 and SEQ ID NO:33), Pfuturbo Hotstart DNA Polymerase (Stratagene) as the enzyme, and the pLenti4/V5-GW/lacZ (Invitrogen) vector attached to the kit as the template under the following conditions (10) to (12).
(10) 95° C. 2 minutes
(11) 95° C. 30 seconds—56° C. 30 seconds—72° C. 3 minutes in 35 cycles
(12) 72° C. 5 minutes Using the same method as that used to prepare the mFBL2-pCR-BluntII-TOPO vector in (2) above, the LacZ-pCR-BluntII-TOPO vector was obtained. Each of the LacZ-pCR-BluntII-TOPO vector and the lentivirus expression vector CSII-CMV-MCS was digested with the restriction endonucleases NotI and NheI (both produced by Takara Shuzo), after which the CSII-CMV-MCS-LacZ vector was obtained by the same method as that used to prepare the CSII-CMV-MCS-mFBL2 vector.

(4) Preparation of FBL2 and LacZ expression Lentivirus

Lentivirus was prepared by the method described below.

HEK293T cells were sown to poly-L-lysine coated 10 cm Petri dishes (IWAKI) at 50000000 cells/dish, and cultured at 37° C. for 18 hours. A total volume of 450 µl of an aqueous solution containing 17 µg of the CSII-CMV-MCS-mFBL2 vector prepared in (2) above, 10 µg of the packaging plasmid pCAG-HIVgp vector, and 10 µg of the envelop plasmid pCMV-VSV-G-RSV-Rev vector, was prepared. For positive control, the CSII-CMV-MCS-LacZ vector prepared in (3) above was used in place of the CSII-CMV-MCS-mFBL2 vector. To each of these CSII-CMV-MCS-mFBL2 aqueous solution and CSII-CMV-MCS-LacZ aqueous solution, 50 µl of 2.5 M $CaCl_2$ was added, after which 500 µl of 2xBBS (50 mM BES, 280 mM NaCl, 1.5 mM $Na_2HPO_4$) was added and mixed, and they were reacted at room temperature for 20 minutes. The mixed liquid obtained was added to the cell-sown 10 cm Petri dish, and the cells were cultured at 37° C. in the presence of 3% $CO_2$ for 16 hours, after which the medium was exchanged with 7.5 ml of a DMEM medium comprising 10 µM forskolin (Sigma), and the cells were further cultured at 37° C. in the presence of 10% $CO_2$ for 48 hours. The culture supernatant was filtered through a 0.45 µm filter and ultracentrifuged at 19,400 rpm, 20° C. for 2 hours; the precipitate obtained was dissolved in HBSS to yield an mFBL2 expression lentivirus and LacZ expression lentivirus.

(5) Measurement of Aβ Contents

Primary nerve cells were prepared from the cerebral cortex of 14-day-old fetal ICR mouse (CHARLES RIVER LABORATORIES JAPAN, INC.), suspended in NeuroBasal™ medium (GIBCO Invitrogen Corporation) at 200,000 cells/ml, seeded at 1 ml per well on poly-L-lysine-coated 24-well plates and cultured at 37° C. for 8 days. Five hundred microliters of the culture supernatant was exchanged, an mFBL2-expressing lentivirus obtained above and lacZ-expressing lentivirus as a control were added to obtain an Moi of 5 for each and then the cells were cultured at 37° C. for 4 days. The culture supernatant was entirely removed, 1 ml of fresh medium was added and the cells were cultured at 37° C. for 3 days. After the cultivation, 100 µl of the culture supernatant was used to determine Aβ contents in the supernatant according to a method of Example 1.

The results are shown below.

The Aβ40 and Aβ42 contents in the culture supernatant of the control (cells added with lacZ-expressing lentivirus) were 342.2±52.05 µM and 50.12±5.20 µM, respectively, whereas the Aβ40 and Aβ42 contents in the culture supernatant of the cells added with mFBL2-expressing lentivirus were 267.7±23.66 pM and 40.86±2.40 pM, respectively.

These results reveal that an overexpression of mFBL2 gene in primary nerve cells derived from mouse cerebral cortex reduces Aβ40 and Aβ42 contents.

Example 6

Intracellular Aβ Production Reducing Action of FBL2

The Neuro2a stable expression strain showing overexpression of the Amyloid precursor protein (APP) gene incorporating a swedish type mutation (obtained from the University of Tokyo), suspended in a DMEM medium comprising 10% FBS at 80000 cells/ml, was sown to 6 cm Petri dishes (Falcon) at 5 ml per dish, the mFBL2 expression lentivirus prepared in Example 5 was simultaneously added to obtain an Moi of 10, and the cells were cultured at 37° C. for 3 days. For control, the LacZ expression lentivirus was used in place of the mFBL2 expression lentivirus, and the cells were cultured in the same manner. The culture supernatants of these culture broths were removed, and the cells were washed with 5 ml PBS three times, after which 550 µl of RIPA buffer (0.5% sodium deoxycholate, 0.1% SDS, 1% NP40, 5 mM EDTA, 50 mM Tris-HCl, 150 mM NaCl, 1 mM β-mercaptoethanol, protease inhibitor cocktail (Roche)) was added, and the cells were disrupted by sonication. Using 100 µl of the supernatant obtained by centrifugation, intracellular Aβ contents were measured according to the method of Example 1. Furthermore, the protein content in the supernatant was measured using a protein assay (Bio-Rad), and intracellular Aβ contents were corrected using the protein content obtained.

The results are shown below.

The Aβ 40 content in the control cells (cells having LacZ expression lentivirus added thereto) was 27.40±3.87 fmol/mg. By contrast, the Aβ 40 content in the cells having the mFBL2 expression lentivirus added thereto was 19.26±0.84 fmol/mg.

From this, it was found that intracellular Aβ 40 contents decreased with overexpression of the mFBL2 gene in the swAPP overexpression Neuro2a stable expression strain.

Example 7

APP-CTF Ubiquitination Promoting Action of FBL2

HEK293A cells suspended in a DMEM medium comprising 10% FBS and non-essential amino acids at 180000 cells/ml were sown to a type I collagen coated 24-well plate (IWAKI) at 500 µl per well, and cultured at 37° C. for 18 hours. 2 µl of lipofectamine 2000 (Invitrogen) was added to 50 µl of OPTI-MEM medium (GIBCO), and the mixture was allowed to stand at room temperature for 5 minutes, after which the mixture was mixed with 50 µl of an OPTI-MEM medium supplemented with 0.5 µg of each of the hAPP695 expression vector (Example 1) and the hFBL2 expression vector (Example 1), and they were reacted at room temperature for 20 minutes. For positive control, the pcDNA3.1-V5/His-LacZ vector (Invitrogen) was used in place of the hFBL2 expression vector, and was mixed with an OPTI-MEM medium supplemented with lipofectamine 2000 in the same manner, and they were reacted at room temperature for 20 minutes. After the reaction, the mixed liquid prepared above was added to the cell-sown plate, the cells were cultured at 37° C. for 4 hours, and the entire quantity of the medium was exchanged with a fresh supply, after which the cells were further cultured for 18 hours. To inhibit the degradation via the ubiquitine-proteasome pathway, the proteasome inhibitor MG132 (CALBIOCHEM) was added to obtain a final concentration of 15 µM, and the cells were cultured at 37° C. for 5 hours. The medium was removed, and the cells were washed with 500 µl of PBS, after which 120 µl of cell disruption buffer solution [50 mM Tris-HCl (pH 7.5), 150 mM NaCl, 1% Triton-X, 1 mM β-mercaptoethanol, protease inhibitor cocktail (Roche), 25 µM MG132] was added, and the cells were disrupted by sonication. To three wells of the supernatant recovered by centrifugation, 25 µl of protein G Sepharose (Zymed Laboratories), previously equilibrated with cell disruption buffer solution, and 2 µg of anti-APP antibody (CT695: Zymed Laboratories) were added, and they were reacted at 4° C. for 3 hours while rotating. After the plate was washed with 1 ml of the cell disruption buffer solution four times, 80 µl of sample buffer solution (Daiichi Kagaku) was added, and the sample was treated at 95° C. for 5 minutes. The sample treated was subjected to SDS-polyacrylamide gel electrophoresis and then transferred onto a PVDF membrane (Millipore), and blocking was performed at room temperature for 1.5 hours [50 mM Tris-HCl (pH 7.5), 150 mM NaCl, 5% skimmed milk, 0.1% Tween], after which a primary antibody [anti-ubiquitin antibody (P4D1: Santa Cruz Biotechnology, 1/500 diluted) or an anti-APP antibody (CT695: Zymed Laboratories, 1/1000 diluted)] was added, and they were reacted at 4° C. for 20 hours. After the primary antibody reaction, the membrane was washed with TTBS buffer [50 mM Tris-HCl (pH 7.5), 150 mM NaCl, 0.1% Tween] three times, a secondary antibody [anti-mouse-HRP antibody (Amersham Biosciences) or an anti-rabbit-HRP antibody (Santa Cruz Biotechnology): 1/2000 diluted] was added, and they were reacted at room temperature for 1.5 hours. After the reaction, the membrane was washed with the TTBS buffer three times, and detection was performed using the ECL plus reagent (Amersham Biosciences).

As a result, in the immunoprecipitated fraction with overexpression of FBL2, compared to the immunoprecipitated fraction with overexpression of the positive control LacZ, an increase in the amount of ubiquitinated protein was observed. Furthermore, only in the immunoprecipitated fraction with expression of FBL2, a band was detected in the high molecular region of CTF; because this band shared the same molecular weight as that of the band from ubiquitinated protein increased by introduction of FBL2, it was found that FBL2 promoted the ubiquitination of CTF.

Example 8

Detection of FBL2 Protein Contents by Cell Immunostaining Method

Primary neurocytes were prepared from the cerebral cortex of an SD rat at 17 days of viviparity (Clea Japan), and suspended in NeuroBasal medium (GIBCO) at 100000 cells/ml, and this suspension was sown to a poly-L-lysine-coated 96-well plate (Sumitomo Bakelite) at 150 µl per well and cultured at 37° C. for 7 days. The mFBL2 expression lentivirus (Example 5) was added to obtain Moi levels of 1, 5 and 10, and the cells were cultured at 37° C. for 4 days. The cells after cultivation were once washed with PBS, after which 4% para-formaldehyde was added, and immobilization was performed at room temperature for 10 minutes. The cells were washed with PBS three times, a PBS containing 1% BSA and 0.1% Triton X was added, and blocking was performed at room temperature for 30 minutes. An anti-FBL2 rabbit polyclonal antibody (human type FBL2 recombinant protein used as the antigen: preparation requested to MBL Company) was diluted 1/500 fold with a PBS containing 1% BSA and 0.1% Triton X, and added to the above-described immobilized cells, and they were reacted at room temperature for 2 hours, after which the cells were washed with PBS three times. Next, Alexa Fluoro 546 goat anti-rabbit IgG (H+L) (Molecular Probes), previously diluted 1/500 fold with a PBS containing 1% BSA and 0.1% Triton X, was added, the mixture was allowed to stand at room temperature for 1 hour, and the cells were washed with PBS three times, after which a fluorescent image was acquired using Discovery-1 (Molecular Devices), and the total fluorescence intensity (Total Intensity) of the positively stained portion was output and analyzed using MetaMorph (Molecular Devices).

The results are shown below.

For the cells not transfected with the mFBL2 expression lentivirus, total fluorescence intensity was 2983.56, whereas for the cells having the mFBL2 expression lentivirus added thereto to obtain Moi levels of 1, 5 and 10, total fluorescence intensity was 17493.27, 34021.35 and 46593.58, respectively. From this result, it was demonstrated that by a cell immunostaining method using an anti-FBL2 antibody, increased expression of the FBL2 protein could be detected. Hence, using this system, screening for a compound that has an action to promote the expression of FBL2 or a salt thereof can be performed.

INDUSTRIAL APPLICABILITY (i) A compound that promotes the ubiquitination of a protein comprising the same or substantially the same amino acid sequence as the amino acid sequence shown by SEQ ID NO:1, SEQ ID NO:2 or SEQ ID NO:3 or a partial peptide thereof or a salt thereof (the protein of the present invention), or a salt thereof, (ii) a compound that promotes the degradation of the protein of the present invention by proteasome, or a salt thereof, (iii) a compound that promotes the binding of a protein comprising a protein comprising the same or substantially the same amino acid sequence as the amino acid sequence shown by SEQ ID NO:23 or a partial peptide thereof or a salt thereof (e.g., SCF complex) and the protein of the present invention, or a salt thereof, (iv) a compound that promotes the expression of a protein comprising the same or substantially the same amino acid sequence as the amino acid sequence shown by SEQ ID NO:23 or a partial peptide thereof or a salt thereof (e.g., FBL2), or a salt thereof, (v) a compound that promotes the expression of a polynucleotide that encodes the gene for a protein comprising the same or substantially the same amino acid sequence as the amino acid sequence shown by SEQ ID NO:23 or a partial peptide thereof (e.g., FBL2), or a salt thereof, and the like can be used as, for example, less toxic safe prophylactic/therapeutic agents for neurodegenerative diseases [e.g., Alzheimer's disease (familial Alzheimer's disease, juvenile Alzheimer's disease, solitary Alzheimer's disease and the like) and the like] and the like.

(vi) A protein comprising the same or substantially the same amino acid sequence as the amino acid sequence shown by SEQ ID NO:1, SEQ ID NO:2 or SEQ ID NO:3 or a partial peptide thereof or a salt thereof (the protein of the present invention), (vii) a protein comprising the same or substantially the same amino acid sequence as the amino acid sequence shown by SEQ ID NO:23 or a partial peptide thereof or a salt thereof (e.g., FBL2), (viii) a protein comprising a protein comprising the same or substantially the same amino acid sequence as the amino acid sequence shown by SEQ ID NO:23 or a partial peptide thereof or a salt thereof (e.g., SCF complex) and the like are useful for screening for a compound having prophylactic/therapeutic action on neurodegenerative diseases [e.g., Alzheimer's disease (familial Alzheimer's disease, juvenile Alzheimer's disease, solitary Alzheimer's disease and the like) and the like] and the like, or a salt thereof.

The invention claimed is:

1. A screening method for a compound or a salt thereof that promotes the binding of (a) a complex comprising a protein comprising an amino acid sequence at least 50% identical to SEQ ID NO: 23 or a partial peptide or salt thereof; and (b) a protein comprising an amino acid sequence at least 50% identical to SEQ ID NO: 1, SEQ ID NO: 2 or SEQ ID NO: 3 or a partial peptide or salt thereof, comprising:
   (I) providing cultures of cells which express the protein (b); (II) contacting some of the cultures with a test compound; (III) precipitating the complex (a) from the cultures; (IV) measuring the amounts of protein (b) co-precipitated with the complex (a) in the presence and absence of the test compound; and (V) comparing the measurement in the presence of the test compound with the measurement in the absence of the test compound, wherein a 20% or greater increase in co-precipitation in the presence of the test compound indicates that the test compound promotes the binding of (a) and (b).

2. The screening method of claim 1, wherein the complex (a) is an SCF complex.

3. A screening method for a compound or a salt thereof that promotes the binding of (a) a protein comprising an amino acid sequence at least 50% identical to SEQ ID NO: 23 or a partial peptide or salt thereof; and (b) a protein comprising an amino acid sequence at least 50% identical to SEQ ID NO: 1, SEQ ID NO: 2 or SEQ ID NO: 3 or a partial peptide or salt thereof, comprising:
   (I) providing cultures of cells which express the protein (b); (II) contacting some of the cultures with a test compound; (III) precipitating the protein (a) from the cultures; (IV) measuring the amounts of protein (b) co-precipitated with the protein (a) in the presence and absence of the test compound; and (V) comparing the measurement in the presence of the test compound with the measurement in the absence of the test compound, wherein a 20% or greater increase in co-precipitation in the presence of the test compound indicates that the test compound promotes the binding of (a) and (b).

* * * * *

SEQUENCE LISTING

<160> NUMBER OF SEQ ID NOS: 35

<210> SEQ ID NO 1
<211> LENGTH: 83
<212> TYPE: PRT
<213> ORGANISM: Homo Sapience

<400> SEQUENCE: 1

Leu Val Phe Phe Ala Glu Asp Val Gly Ser Asn Lys Gly Ala Ile Ile
                 5                  10                  15

Gly Leu Met Val Gly Gly Val Val Ile Ala Thr Val Ile Val Ile Thr
             20                  25                  30

Leu Val Met Leu Lys Lys Lys Gln Tyr Thr Ser Ile His His Gly Val
         35                  40                  45

Val Glu Val Asp Ala Ala Val Thr Pro Glu Glu Arg His Leu Ser Lys
     50                  55                  60

Met Gln Gln Asn Gly Tyr Glu Asn Pro Thr Tyr Lys Phe Phe Glu Gln
 65                  70                  75                  80

Met Gln Asn

<210> SEQ ID NO 2
<211> LENGTH: 99
<212> TYPE: PRT
<213> ORGANISM: Homo Sapience

<400> SEQUENCE: 2

Asp Ala Glu Phe Arg His Asp Ser Gly Tyr Glu Val His His Gln Lys
                 5                  10                  15

Leu Val Phe Phe Ala Glu Asp Val Gly Ser Asn Lys Gly Ala Ile Ile
             20                  25                  30

Gly Leu Met Val Gly Gly Val Val Ile Ala Thr Val Ile Val Ile Thr
         35                  40                  45

Leu Val Met Leu Lys Lys Lys Gln Tyr Thr Ser Ile His His Gly Val
     50                  55                  60

Val Glu Val Asp Ala Ala Val Thr Pro Glu Glu Arg His Leu Ser Lys
 65                  70                  75                  80

Met Gln Gln Asn Gly Tyr Glu Asn Pro Thr Tyr Lys Phe Phe Glu Gln
                 85                  90                  95

Met Gln Asn

<210> SEQ ID NO 3
<211> LENGTH: 695
<212> TYPE: PRT
<213> ORGANISM: Homo Sapience

<400> SEQUENCE: 3

Met Leu Pro Gly Leu Ala Leu Leu Leu Leu Ala Ala Trp Thr Ala Arg
                 5                  10                  15

Ala Leu Glu Val Pro Thr Asp Gly Asn Ala Gly Leu Leu Ala Glu Pro
             20                  25                  30

Gln Ile Ala Met Phe Cys Gly Arg Leu Asn Met His Met Asn Val Gln
         35                  40                  45

Asn Gly Lys Trp Asp Ser Asp Pro Ser Gly Thr Lys Thr Cys Ile Asp
     50                  55                  60

Thr Lys Glu Gly Ile Leu Gln Tyr Cys Gln Glu Val Tyr Pro Glu Leu
 65                  70                  75                  80

-continued

```
Gln Ile Thr Asn Val Val Glu Ala Asn Gln Pro Val Thr Ile Gln Asn
                85                  90                  95
Trp Cys Lys Arg Gly Arg Lys Gln Cys Lys Thr His Pro His Phe Val
            100                 105                 110
Ile Pro Tyr Arg Cys Leu Val Gly Glu Phe Val Ser Asp Ala Leu Leu
        115                 120                 125
Val Pro Asp Lys Cys Lys Phe Leu His Gln Glu Arg Met Asp Val Cys
    130                 135                 140
Glu Thr His Leu His Trp His Thr Val Ala Lys Glu Thr Cys Ser Glu
145                 150                 155                 160
Lys Ser Thr Asn Leu His Asp Tyr Gly Met Leu Leu Pro Cys Gly Ile
                165                 170                 175
Asp Lys Phe Arg Gly Val Glu Phe Val Cys Cys Pro Leu Ala Glu Glu
            180                 185                 190
Ser Asp Asn Val Asp Ser Ala Asp Ala Glu Glu Asp Asp Ser Asp Val
        195                 200                 205
Trp Trp Gly Gly Ala Asp Thr Asp Tyr Ala Asp Gly Ser Glu Asp Lys
    210                 215                 220
Val Val Glu Val Ala Glu Glu Glu Val Ala Glu Val Glu Glu Glu Glu
225                 230                 235                 240
Glu Ala Asp Asp Asp Glu Asp Asp Glu Asp Gly Asp Glu Val Glu Glu
                245                 250                 255
Glu Ala Glu Glu Pro Tyr Glu Glu Ala Thr Glu Arg Thr Thr Ser Ile
            260                 265                 270
Ala Thr Thr Thr Thr Thr Thr Glu Ser Val Glu Glu Val Val Arg
        275                 280                 285
Val Pro Thr Thr Ala Ala Ser Thr Pro Asp Ala Val Asp Lys Tyr Leu
    290                 295                 300
Glu Thr Pro Gly Asp Glu Asn Glu His Ala His Phe Gln Lys Ala Lys
305                 310                 315                 320
Glu Arg Leu Glu Ala Lys His Arg Glu Arg Met Ser Gln Val Met Arg
                325                 330                 335
Glu Trp Glu Glu Ala Glu Arg Gln Ala Lys Asn Leu Pro Lys Ala Asp
            340                 345                 350
Lys Lys Ala Val Ile Gln His Phe Gln Glu Lys Val Glu Ser Leu Glu
        355                 360                 365
Gln Glu Ala Ala Asn Glu Arg Gln Gln Leu Val Glu Thr His Met Ala
    370                 375                 380
Arg Val Glu Ala Met Leu Asn Asp Arg Arg Arg Leu Ala Leu Glu Asn
385                 390                 395                 400
Tyr Ile Thr Ala Leu Gln Ala Val Pro Pro Arg Pro Arg His Val Phe
                405                 410                 415
Asn Met Leu Lys Lys Tyr Val Arg Ala Glu Gln Lys Asp Arg Gln His
            420                 425                 430
Thr Leu Lys His Phe Glu His Val Arg Met Val Asp Pro Lys Lys Ala
        435                 440                 445
Ala Gln Ile Arg Ser Gln Val Met Thr His Leu Arg Val Ile Tyr Glu
    450                 455                 460
Arg Met Asn Gln Ser Leu Ser Leu Leu Tyr Asn Val Pro Ala Val Ala
465                 470                 475                 480
Glu Glu Ile Gln Asp Glu Val Asp Glu Leu Leu Gln Lys Glu Gln Asn
                485                 490                 495
Tyr Ser Asp Asp Val Leu Ala Asn Met Ile Ser Glu Pro Arg Ile Ser
            500                 505                 510
```

```
Tyr Gly Asn Asp Ala Leu Met Pro Ser Leu Thr Glu Thr Lys Thr Thr
        515                 520                 525
Val Glu Leu Leu Pro Val Asn Gly Glu Phe Ser Leu Asp Asp Leu Gln
    530                 535                 540
Pro Trp His Ser Phe Gly Ala Asp Ser Val Pro Ala Asn Thr Glu Asn
545                 550                 555                 560
Glu Val Glu Pro Val Asp Ala Arg Pro Ala Asp Arg Gly Leu Thr
                565                 570                 575
Thr Arg Pro Gly Ser Gly Leu Thr Asn Ile Lys Thr Glu Glu Ile Ser
            580                 585                 590
Glu Val Lys Met Asp Ala Glu Phe Arg His Asp Ser Gly Tyr Glu Val
        595                 600                 605
His His Gln Lys Leu Val Phe Phe Ala Glu Asp Val Gly Ser Asn Lys
    610                 615                 620
Gly Ala Ile Ile Gly Leu Met Val Gly Val Val Ile Ala Thr Val
625                 630                 635                 640
Ile Val Ile Thr Leu Val Met Leu Lys Lys Lys Gln Tyr Thr Ser Ile
                645                 650                 655
His His Gly Val Val Glu Val Asp Ala Ala Val Thr Pro Glu Glu Arg
            660                 665                 670
His Leu Ser Lys Met Gln Gln Asn Gly Tyr Glu Asn Pro Thr Tyr Lys
        675                 680                 685
Phe Phe Glu Gln Met Gln Asn
    690                 695

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
ctgtcagaga atgacacagc acctgcacag                                    30

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
taatacgact cactataggg                                               20

<210> SEQ ID NO 6
<211> LENGTH: 18
<212> TYPE: DNA
<213> ORGANISM: Artificial Sequence
<220> FEATURE:
<223> OTHER INFORMATION: Primer

<400> SEQUENCE: 6
tagaaggcac agtcgagg                                                 18

<210> SEQ ID NO 7
<211> LENGTH: 22
<212> TYPE: RNA
<213> ORGANISM: Artificial Sequence
<220> FEATURE:
<223> OTHER INFORMATION: siRNA
```

```
<400> SEQUENCE: 7
gcaaggugac ccugaaguuc au                                             22

<210> SEQ ID NO 8
<211> LENGTH: 19
<212> TYPE: RNA
<213> ORGANISM: Artificial Sequence
<220> FEATURE:
<223> OTHER INFORMATION: siRNA

<400> SEQUENCE: 8
ccucacagau gcccucuu                                                  19

<210> SEQ ID NO 9
<211> LENGTH: 58
<212> TYPE: DNA
<213> ORGANISM: Artificial Sequence
<220> FEATURE:
<223> OTHER INFORMATION: Primer

<400> SEQUENCE: 9
caccatggat tacaaggatg acgacgataa gatggttttc tcaaacaatg atgaaggc     58

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10
atccatatgg ttttctcaaa caatgatgaa                                     30

<210> SEQ ID NO 11
<211> LENGTH: 30
<212> TYPE: DNA
<213> ORGANISM: Artificial Sequence
<220> FEATURE:
<223> OTHER INFORMATION: Primer

<400> SEQUENCE: 11
ctactgcagt cagagaatga cacagcacct                                     30

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
cgatgatgaa gatacccccac c                                             21

<210> SEQ ID NO 13
<211> LENGTH: 30
<212> TYPE: DNA
<213> ORGANISM: Artificial Sequence
<220> FEATURE:
<223> OTHER INFORMATION: Primer

<400> SEQUENCE: 13
caccatgcct tcaattaagt tgcagagttc                                     30

<210> SEQ ID NO 14
<211> LENGTH: 30
```

```
<212> TYPE: DNA
<213> ORGANISM: Artificial Sequence
<220> FEATURE:
<223> OTHER INFORMATION: Primer

<400> SEQUENCE: 14
atttcacttc tcttcacacc actggttctc                              30

<210> SEQ ID NO 15
<211> LENGTH: 30
<212> TYPE: DNA
<213> ORGANISM: Artificial Sequence
<220> FEATURE:
<223> OTHER INFORMATION: Primer

<400> SEQUENCE: 15
caccatggtg aaaatgacaa agtccaaaac                              30

<210> SEQ ID NO 16
<211> LENGTH: 30
<212> TYPE: DNA
<213> ORGANISM: Artificial Sequence
<220> FEATURE:
<223> OTHER INFORMATION: Primer

<400> SEQUENCE: 16
acattactcc cagccattgt ctttgatcat                              30

<210> SEQ ID NO 17
<211> LENGTH: 30
<212> TYPE: DNA
<213> ORGANISM: Artificial Sequence
<220> FEATURE:
<223> OTHER INFORMATION: Primer

<400> SEQUENCE: 17
atcggattca tggtgaaaat gacaaagtcc                              30

<210> SEQ ID NO 18
<211> LENGTH: 30
<212> TYPE: DNA
<213> ORGANISM: Artificial Sequence
<220> FEATURE:
<223> OTHER INFORMATION: Primer

<400> SEQUENCE: 18
ctactcgagt tactcccagc cattgtcttt                              30

<210> SEQ ID NO 19
<211> LENGTH: 28
<212> TYPE: DNA
<213> ORGANISM: Artificial Sequence
<220> FEATURE:
<223> OTHER INFORMATION: Primer

<400> SEQUENCE: 19
caccatgttt tctcaaacaa tgatgagg                                28

<210> SEQ ID NO 20
<211> LENGTH: 249
<212> TYPE: DNA
<213> ORGANISM: Homo Sapience

<400> SEQUENCE: 20
ttggtgttct ttgcagaaga tgtgggttca aacaaaggtg caatcattgg actcatggtg     60
ggcggtgttg tcatagcgac agtgatcgtc atcaccttgg tgatgctgaa gaagaaacag    120
```

```
tacacatcca ttcatcatgg tgtggtggag gttgacgccg ctgtcacccc agaggagcgc      180
cacctgtcca agatgcagca gaacggctac gaaaatccaa cctacaagtt ctttgagcag      240
atgcagaac                                                              249
```

<210> SEQ ID NO 21
<211> LENGTH: 297
<212> TYPE: DNA
<213> ORGANISM: Homo Sapience

<400> SEQUENCE: 21

```
gatgcagaat tccgacatga ctcaggatat gaagttcatc atcaaaaatt ggtgttcttt       60
gcagaagatg tgggttcaaa caaggtgca atcattggac tcatggtggg cggtgttgtc      120
atagcgacag tgatcgtcat caccttggtg atgctgaaga agaaacagta cacatccatt     180
catcatggtg tggtggaggt tgacgccgct gtcaccccag aggagcgcca cctgtccaag     240
atgcagcaga acggctacga aaatccaacc tacaagttct tgagcagat gcagaac         297
```

<210> SEQ ID NO 22
<211> LENGTH: 2085
<212> TYPE: DNA
<213> ORGANISM: Homo Sapience

<400> SEQUENCE: 22

```
atgctgcccg gtttggcact gctcctgctg ccgcctggga cggctcgggc gctggaggta       60
cccactgatg gtaatgctgg cctgctggct gaacccagag ttgccatgtt ctgtggcaga     120
ctgaacatgc acatgaatgt ccagaatggg aagtgggatt cagatccatc agggaccaaa     180
acctgcattg taccaaggaa aggcatcctg cagtattgcc aagaagtcta ccctgaactg     240
cagatcacca atgtggtaga agccaaccaa ccagtgacca tccagaactg gtgcaagcgg     300
ggccgcaagc agtgcaagac catccccac tttgtgattc cctaccgctg cttagttggt     360
gagtttgtaa gtgatgccct tctcgttcct gacaagtgca aattcttaca ccaggagagg     420
atggatgttt gcgaaactca tcttcactgg cacaccgtcg ccaaagagac atgcagtgag     480
aagagtacca acttgcatga ctacggcatg ttgctgccct gcggaattga caagttccga     540
ggggtagagt ttgtgtgttg cccactggct gaagaaagtg acaatgtgga ttctgctgat     600
gcggaggagg atgactcgga tgtctggtgg ggcggagcag acacagacta tgcagatggg     660
agtgaagaca aagtagtaga agtagcgagg aggaagaag tggctgaggt ggaagaagaa     720
gaagccgatg atgacgagga cgatgaggat ggtgatgagg tagaggaaga ggctgaggaa     780
ccctacgaag aagccacaga gagaaccacc agcattgcca ccaccaccac caccaccaca     840
gagtctgtgg aagaggtggt tcgagttcct acaacagcag ccagtacccc tgatgccgtt     900
gacaagtatc tcgagacacc tggggatgag aatgaacatg cccatttcca gaaagccaaa     960
gagaggcttg aggccaagca ccgagagaga atgtcccagg tcatgagaga atgggaagag    1020
gcagaacgtc aagcaaagaa cttgcctaaa gctgataaga aggcagttat ccagcatttc    1080
caggagaaag tggaatcttt ggaacaggaa gcagccaacg agacagca gctggtggag    1140 acacacatgg ccagagtgga agccatgctc aatgaccgcc gccgcctggc cctggagaac    1200
tacatcaccg ctctgcaggc tgttcctcct cggcctcgtc acgtgttcaa tatgctaaag    1260
aagtatgtcc gcgcagaaca gaaggacaga cagcacaccc taaagcattt cgagcatgtg    1320 cgcatggtg atcccaagaa agccgctcag atccggtccc aggttatgac acacctccgt    1380
gtgatttatg agcgcatgaa tcagtctctc tccctgctct acaacgtgcc tgcagtggcc    1440
```

```
gaggagattc aggatgaagt tgatgagctg cttcagaaag agcaaaacta ttcagatgac    1500
gtcttggcca acatgattag tgaaccaagg atcagttacg gaaacgatgc tctcatgcca    1560
tctttgaccg aaacgaaaac caccgtggag ctccttcccg tgaatggaga gttcagcctg    1620
gacgatctcc agccgtggca ttcttttggg gctgactctg tgccagccaa cacagaaaac    1680
gaagttgagc ctgttgatgc ccgccctgct gccgaccgag gactgaccac tcgaccaggt    1740
tctgggttga caaatatcaa gacggaggag atctctgaag tgaagatgga tgcagaattc    1800
cgacatgact caggatatga agttcatcat caaaaattgg tgttctttgc agaagatgtg    1860
ggttcaaaca aaggtgcaat cattggactc atggtgggcg tgttgtcat agcgacagtg    1920 atcgtcatca ccttggtgat gctgaagaag aaacagtaca catccattca tcatggtgtg    1980
gtggaggttg acgccgctgt caccccagag gagcgccacc tgtccaagat gcagcagaac    2040
ggctacgaaa atccaaccta caagttcttt gagcagatgc agaac                    2085
```

<210> SEQ ID NO 23
<211> LENGTH: 423
<212> TYPE: PRT
<213> ORGANISM: Homo Sapience

<400> SEQUENCE: 23

```
Met Val Phe Ser Asn Asn Asp Glu Gly Leu Ile Asn Lys Lys Leu Pro
                5                   10                  15

Lys Glu Leu Leu Leu Arg Ile Phe Ser Phe Leu Asp Ile Val Thr Leu
            20                  25                  30

Cys Arg Cys Ala Gln Ile Ser Lys Ala Trp Asn Ile Leu Ala Leu Asp
        35                  40                  45

Gly Ser Asn Trp Gln Arg Ile Asp Leu Phe Asn Phe Gln Thr Asp Val
    50                  55                  60

Glu Gly Arg Val Val Glu Asn Ile Ser Lys Arg Cys Gly Gly Phe Leu
65                  70                  75                  80

Arg Lys Leu Ser Leu Arg Gly Cys Ile Gly Val Gly Asp Ser Ser Leu
                85                  90                  95

Lys Thr Phe Ala Gln Asn Cys Arg Asn Ile Glu His Leu Asn Leu Asn
            100                 105                 110

Gly Cys Thr Lys Ile Thr Asp Ser Thr Cys Tyr Ser Leu Ser Arg Phe
        115                 120                 125

Cys Ser Lys Leu Lys His Leu Asp Leu Thr Ser Cys Val Ser Ile Thr
    130                 135                 140

Asn Ser Ser Leu Lys Gly Ile Ser Glu Gly Cys Arg Asn Leu Glu Tyr
145                 150                 155                 160

Leu Asn Leu Ser Trp Cys Asp Gln Ile Thr Lys Asp Gly Ile Glu Ala
                165                 170                 175

Leu Val Arg Gly Cys Arg Gly Leu Lys Ala Leu Leu Leu Arg Gly Cys
            180                 185                 190

Thr Gln Leu Glu Asp Glu Ala Leu Lys His Ile Gln Asn Tyr Cys His
        195                 200                 205

Glu Leu Val Ser Leu Asn Leu Gln Ser Cys Ser Arg Ile Thr Asp Glu
    210                 215                 220

Gly Val Val Gln Ile Cys Arg Gly Cys His Arg Leu Gln Ala Leu Cys
225                 230                 235                 240

Leu Ser Gly Cys Ser Asn Leu Thr Asp Ala Ser Leu Thr Ala Leu Gly
                245                 250                 255

Leu Asn Cys Pro Arg Leu Gln Ile Leu Glu Ala Ala Arg Cys Ser His
```

```
                260              265              270
Leu Thr Asp Ala Gly Phe Thr Leu Leu Ala Arg Asn Cys His Glu Leu
            275                 280                 285

Glu Lys Met Asp Leu Glu Glu Cys Ile Leu Ile Thr Asp Ser Thr Leu
        290                 295                 300

Ile Gln Leu Ser Ile His Cys Pro Lys Leu Gln Ala Leu Ser Leu Ser
305                 310                 315                 320

His Cys Glu Leu Ile Thr Asp Asp Gly Ile Leu His Leu Ser Asn Ser
                325                 330                 335

Thr Cys Gly His Glu Arg Leu Arg Val Leu Glu Leu Asp Asn Cys Leu
            340                 345                 350

Leu Ile Thr Asp Val Ala Leu Glu His Leu Glu Asn Cys Arg Gly Leu
        355                 360                 365

Glu Arg Leu Glu Leu Tyr Asp Cys Gln Gln Val Thr Arg Ala Gly Ile
    370                 375                 380

Lys Arg Met Arg Ala Gln Leu Pro His Val Lys Val His Ala Tyr Phe
385                 390                 395                 400

Ala Pro Val Thr Pro Pro Thr Ala Val Ala Gly Ser Gly Gln Arg Leu
                405                 410                 415

Cys Arg Cys Cys Val Ile Leu
            420

<210> SEQ ID NO 24
<211> LENGTH: 1269
<212> TYPE: DNA
<213> ORGANISM: Homo Sapience

<400> SEQUENCE: 24
atggttttct caaacaatga tgaaggcctt attaacaaaa agttacccaa agaacttctg      60
ttaagaatat tttccttctt ggatatagta actttgtgcc gatgtgcaca gatttccaag     120
gcttggaaca tcttagccct ggatggaagc aactggcaaa gaatagatct ttttaacttt     180
caaacagatg tagagggtcg agtggtggaa aatatctcga agcgatgcgg tggattcctg     240
aggaagctca gcttgcgagg ctgcattggt gttgggggatt cctccttgaa gacctttgca     300
cagaactgcc gaaacattga acatttgaac ctcaatggat gcacaaaaat cactgacagc     360
acgtgttata gccttagcag attctgttcc aagctgaaac atctggatct gacctcctgt     420
gtgtctatta caaacagctc cttgaagggg atcagtgagg ctgccgaaa cctggagtac     480 ctgaacctct cttggtgtga tcagatcacg aaggatggca tcgaggcact ggtgcgaggt     540
tgtcgaggcc tgaaagccct gctcctgagg ggctgcacac agttagaaga tgaagctctg     600
aaacacattc agaattactg ccatgagctt gtgagcctca acttgcagtc ctgctcacgt     660
atcacggatg aaggtgtggt gcagatatgc aggggctgtc accggctaca ggctctctgc     720
ctttcgggtt gcagcaacct cacagatgcc tctcttacag ccctgggttt gaactgtccg     780
cgactgcaaa ttttggaggc tgcccgatgc tcccatttga ctgacgcagg ttttacactt     840
ttagctcgga attgccacga attggagaag atggatcttg aagaatgcat cctgataacc     900
gacagcacac tcatccagct ctccattcac tgtcctaaac tgcaagccct gagcctgtcc     960
cactgtgaac tcatcacaga tgatgggatc ctgcacctga gcaacagtac ctgtggccat    1020
gagaggctgc gggtactgga gttggacaac tgcctcctca tcactgatgt ggccctggaa    1080
cacctagaga actgccgagg cctggagcgc ctcgagctgt acgactgcca gcaggttacc    1140
cgtgcaggca tcaagcggat gcgggctcag ctccctcatg tcaaagtcca cgcctacttt    1200
```

-continued

```
gctcccgtca ccccaccgac agcagtggca ggaagtggac agcgactgtg caggtgctgt    1260
gtcattctc                                                            1269
```

<210> SEQ ID NO 25
<211> LENGTH: 30
<212> TYPE: DNA
<213> ORGANISM: Artificial
<220> FEATURE:
<223> OTHER INFORMATION: Primer

<400> SEQUENCE: 25

```
caccatggtt ttctcaaaca gtgatgatgg                                       30
```

<210> SEQ ID NO 26
<211> LENGTH: 30
<212> TYPE: DNA
<213> ORGANISM: Artificial
<220> FEATURE:
<223> OTHER INFORMATION: Primer

<400> SEQUENCE: 26

```
ctgtcagagt atgacacagc atctgcacag                                       30
```

<210> SEQ ID NO 27
<211> LENGTH: 19
<212> TYPE: DNA
<213> ORGANISM: Artificial
<220> FEATURE:
<223> OTHER INFORMATION: Primer

<400> SEQUENCE: 27

```
cttccgtgtt tcagttagc                                                   19
```

<210> SEQ ID NO 28
<211> LENGTH: 30
<212> TYPE: DNA
<213> ORGANISM: Artificial
<220> FEATURE:
<223> OTHER INFORMATION: Primer

<400> SEQUENCE: 28

```
catgaattca tggttttctc aaacagtgat                                       30
```

<210> SEQ ID NO 29
<211> LENGTH: 30
<212> TYPE: DNA
<213> ORGANISM: Artificial
<220> FEATURE:
<223> OTHER INFORMATION: Primer

<400> SEQUENCE: 29

```
ctactcgagt cagagtatga cacagcatct                                       30
```

<210> SEQ ID NO 30
<211> LENGTH: 35
<212> TYPE: DNA
<213> ORGANISM: Artificial
<220> FEATURE:
<223> OTHER INFORMATION: Primer

<400> SEQUENCE: 30

```
acgctcgaga tggttttctc aaacagtgat gatgg                                 35
```

<210> SEQ ID NO 31
<211> LENGTH: 38
<212> TYPE: DNA

<213> ORGANISM: Artificial
<220> FEATURE:
<223> OTHER INFORMATION: Primer

<400> SEQUENCE: 31
agtgcggccg ctcagagtat gacacagcat ctgcacag        38

<210> SEQ ID NO 32
<211> LENGTH: 35
<212> TYPE: DNA
<213> ORGANISM: Artificial
<220> FEATURE:
<223> OTHER INFORMATION: Primer

<400> SEQUENCE: 32
gatgctagca tgatagatcc cgtcgtttta caacg        35

<210> SEQ ID NO 33
<211> LENGTH: 36
<212> TYPE: DNA
<213> ORGANISM: Artificial
<220> FEATURE:
<223> OTHER INFORMATION: Primer

<400> SEQUENCE: 33
agtgcggccg ctcatttttg acaccagacc aactgg        36

<210> SEQ ID NO 34
<211> LENGTH: 423
<212> TYPE: PRT
<213> ORGANISM: Mus musculus

<400> SEQUENCE: 34

Met Val Phe Ser Asn Ser Asp Asp Gly Leu Ile Asn Lys Lys Leu Pro
 1               5                  10                  15

Lys Glu Leu Leu Leu Arg Ile Phe Ser Phe Leu Asp Ile Val Thr Leu
                20                  25                  30

Cys Arg Cys Ala Gln Ile Ser Lys Ala Trp Asn Ile Leu Ala Leu Asp
            35                  40                  45

Gly Ser Asn Trp Gln Arg Val Asp Leu Phe Asn Phe Gln Thr Asp Val
        50                  55                  60

Glu Gly Arg Val Val Glu Asn Ile Ser Lys Arg Cys Gly Gly Phe Leu
    65                  70                  75                  80

Arg Lys Leu Ser Leu Arg Gly Cys Ile Gly Val Gly Asp Ser Ser Leu
                85                  90                  95

Lys Thr Phe Ala Gln Asn Cys Arg Asn Ile Glu His Leu Asn Leu Asn
            100                 105                 110

Gly Cys Thr Lys Ile Thr Asp Ser Thr Cys Tyr Ser Leu Ser Arg Phe
        115                 120                 125

Cys Ser Lys Leu Lys His Leu Asp Leu Thr Ser Cys Val Ser Val Thr
    130                 135                 140

Asn Ser Ser Leu Lys Gly Ile Ser Glu Gly Cys Arg Asn Leu Glu Tyr
145                 150                 155                 160

Leu Asn Leu Ser Trp Cys Asp Gln Ile Thr Lys Gly Ile Glu Ala
                165                 170                 175

Leu Val Arg Gly Cys Arg Gly Leu Lys Ala Leu Leu Leu Arg Gly Cys
            180                 185                 190

Thr Gln Leu Glu Asp Glu Ala Leu Lys His Ile Gln Asn His Cys His
        195                 200                 205

Glu Leu Val Ser Leu Asn Leu Gln Ser Cys Ser Arg Ile Thr Asp Asp

```
            210                 215                 220
Gly Val Val Gln Ile Cys Arg Gly Cys His Arg Leu Gln Ala Leu Cys
225                 230                 235                 240

Leu Ser Gly Cys Ser Asn Leu Thr Asp Ala Ser Leu Thr Ala Leu Gly
                245                 250                 255

Leu Asn Cys Pro Arg Leu Gln Val Leu Glu Ala Ala Arg Cys Ser His
                260                 265                 270

Leu Thr Asp Ala Gly Phe Thr Leu Leu Ala Arg Asn Cys His Glu Leu
                275                 280                 285

Glu Lys Met Asp Leu Glu Glu Cys Val Leu Ile Thr Asp Ser Thr Leu
                290                 295                 300

Val Gln Leu Ser Ile His Cys Pro Lys Leu Gln Ala Leu Ser Leu Ser
305                 310                 315                 320

His Cys Glu Leu Ile Thr Asp Glu Gly Ile Leu His Leu Ser Ser Ser
                325                 330                 335

Thr Cys Gly His Glu Arg Leu Arg Val Leu Glu Leu Asp Asn Cys Leu
                340                 345                 350

Leu Val Thr Asp Ala Ser Leu Glu His Leu Glu Asn Cys Arg Gly Leu
                355                 360                 365

Glu Arg Leu Glu Leu Tyr Asp Cys Gln Gln Val Thr Arg Ala Gly Ile
370                 375                 380

Lys Arg Met Arg Ala Gln Leu Pro His Val Lys Val His Ala Tyr Phe
385                 390                 395                 400

Ala Pro Val Thr Pro Pro Ala Val Ala Gly Ser Gly His Arg Leu
                405                 410                 415

Cys Arg Cys Cys Val Ile Leu
                420

<210> SEQ ID NO 35
<211> LENGTH: 1272
<212> TYPE: DNA
<213> ORGANISM: Mus musculus

<400> SEQUENCE: 35
atggttttct caaacagtga tgatggcctt atcaacaaga agctacccaa ggagctcctc        60
ttgagaatat tctccttctt ggacatcgta actctatgcc gatgtgcaca gatctccaag       120
gcctggaaca tcttagccct ggatggcagc aactggcaac gggtggatct tttttaacttc     180 cagacagatg tagagggccg agtggtggaa acatctccaa gaggtgcgg tggcttcctt       240 agaaagctca gcctgcgtgg ctgcatcgga gtcggggact cctctttgaa gacctttgca      300
cagaactgcc ggaacattga acatttaaac ctcaatggct gcacgaaaat cactgacagc      360
acgtgttaca gccttagcag attctgttcc aagctgaaac acctggatct cacgtcctgc      420
gtgtctgtta ccaacagctc tttaaagggc atcagcgagg ctgccggaa cctggaatat      480 ctgaacctct cctggtgtga ccagatcaca aggaaggca ttgaggcgct ggtgcggggg       540 tgccgggtt tgaaagccct gctcctgagg ggttgtacac agttagagga cgaagctctg       600
aaacacattc agaaccactg ccacgagctg gtgagcctca acctgcagtc ctgctcacgc      660
atcactgatg atggcgtggt gcagatctgc agggctgcc accggctaca ggctctgtgc       720
ctctcgggtt gtagcaacct tacgatgca tctctcacag ccttgggcct gaactgcccc       780
agactacaag ttttggaggc tgcccggtgc tccatctga ccgacgcagg ctttacactg       840
ctagctcgga attgccatga gctggagaag atggaccttg aagaatgtgt cctgattacc       900
gacagcaccc tcgtccagct ctccatccac tgtcccaagc tgcaagccct gagcttgtcc      960
```

```
cactgtgagc tcatcacaga tgaggggatc ctgcacctga gcagcagcac ctgtgggcac      1020
gagagactcc gggtgctgga gctggacaac tgccttcttg tcacggacgc ctcgctggag      1080
cacctggaga actgccgagg cctggagcga ctggagcttt acgactgcca gcaggtcacc      1140
cgtgcaggca tcaagcgcat gcgggctcag cttcctcatg tcaaagtcca tgcctacttt      1200
gctccagtca cccctccacc agcagtggca ggaagtggac atcgactgtg cagatgctgt      1260
gtcatactct ga                                                          1272
```